(12) United States Patent
Zullo et al.

(10) Patent No.: US 7,951,232 B2
(45) Date of Patent: *May 31, 2011

(54) SURFACE COATING COMPOSITIONS AND METHODS

(75) Inventors: Jill Louise Zullo, Excelsior, MN (US); James C. Anderson, Eden Prairie, MN (US); Hiroki Kaido, Eden Prairie, MN (US); Richard L. Pederson, San Gabriel, CA (US); Yann Schrodi, Agoura Hills, CA (US); William H. Sperber, Minnetonka, MN (US); Michael J. Tupy, Crystal, MN (US); Earl H. Wagener, Pendleton, SC (US)

(73) Assignee: Elevance Renewable Sciences, Inc., Bolingbrook, IL (US)

( * ) Notice: Subject to any disclaimer, the term of this patent is extended or adjusted under 35 U.S.C. 154(b) by 301 days.

This patent is subject to a terminal disclaimer.

(21) Appl. No.: 11/704,800

(22) Filed: Feb. 9, 2007

(65) Prior Publication Data
US 2007/0227400 A1   Oct. 4, 2007

Related U.S. Application Data

(60) Provisional application No. 60/772,137, filed on Feb. 9, 2006, provisional application No. 60/851,472, filed on Oct. 13, 2006.

(51) Int. Cl.
*C09D 5/14* (2006.01)
*C09D 5/16* (2006.01)
*B05D 5/00* (2006.01)

(52) U.S. Cl. ............. 106/15.05; 106/18.32; 424/78.09; 427/384; 514/506; 514/558; 514/578; 524/176; 524/284; 524/300; 524/315; 524/316

(58) Field of Classification Search ............. 106/15.05, 106/18.32; 427/384; 514/506, 558, 578; 424/78.09; 524/176, 284, 300, 315, 316
See application file for complete search history.

(56) References Cited

U.S. PATENT DOCUMENTS

| | | |
|---|---|---|
| 4,055,662 A | 10/1977 | Kürner |
| 4,097,604 A | 6/1978 | Thiele |
| 4,214,006 A | 7/1980 | Thiele |
| 4,215,144 A | 7/1980 | Thiele |
| 4,224,028 A | 9/1980 | Thiele |
| 4,224,307 A | 9/1980 | Thiele et al. |
| 4,339,462 A | 7/1982 | Muntwyler et al. |
| 4,442,125 A * | 4/1984 | Thiele ............ 514/60 |
| 4,545,941 A | 10/1985 | Rosenburg |
| 4,920,106 A | 4/1990 | Chang et al. |
| 5,464,850 A | 11/1995 | Voo et al. |
| 5,507,970 A | 4/1996 | Ishikawa et al. |
| 5,530,113 A | 6/1996 | Christ et al. |
| 5,612,476 A | 3/1997 | Christ et al. |
| 5,631,218 A | 5/1997 | Allan et al. |
| 5,658,584 A | 8/1997 | Yamaguchi |
| 5,679,341 A | 10/1997 | Cutler et al. |
| 5,725,875 A | 3/1998 | Noll et al. |
| 5,750,733 A | 5/1998 | Vermeer et al. |
| 5,750,815 A | 5/1998 | Grubbs et al. |
| 5,756,718 A | 5/1998 | Christ et al. |
| 5,843,918 A | 12/1998 | Christ et al. |
| 5,853,732 A | 12/1998 | Munden |
| 5,885,554 A | 3/1999 | Michael et al. |
| 5,888,520 A | 3/1999 | Toma et al. |
| 5,919,749 A | 7/1999 | Sakamoto et al. |
| 5,922,863 A | 7/1999 | Grubbs et al. |
| 5,939,080 A | 8/1999 | Michael et al. |
| 6,063,393 A | 5/2000 | Tsuboi et al. |
| 6,080,387 A | 6/2000 | Zhou et al. |
| 6,147,120 A | 11/2000 | Swart et al. |
| 6,165,447 A | 12/2000 | Trivedi et al. |
| 6,278,007 B1 | 8/2001 | Inaoka et al. |
| 6,306,998 B1 | 10/2001 | Kimura et al. |
| 6,413,910 B1 | 7/2002 | Vasiljevich et al. |
| 6,414,097 B1 | 7/2002 | Grubbs et al. |
| 6,468,953 B1 | 10/2002 | Hitchems et al. |
| 6,472,358 B1 | 10/2002 | Richter et al. |
| 6,569,829 B1 | 5/2003 | Yamawaki et al. |
| 6,579,556 B2 | 6/2003 | Kirby et al. |
| 6,593,283 B2 | 7/2003 | Hei et al. |
| 6,599,541 B1 | 7/2003 | Brindavanam et al. |

(Continued)

FOREIGN PATENT DOCUMENTS

CA    2144021    11/1995

(Continued)

OTHER PUBLICATIONS

Patel et al., "High conversion and productive catalyst turnovers in cross-metathesis reactions of natural oils with 2-butene," Green Chemistry, 2006, vol. 8, pp. 450-454.

Unexamined Patent Disclosure Belletin for Japanese Application No. S46-95345, filed Nov. 29, 1971, entitled "Antiseptic and anti-penetration method for food and other materials", by Yuzo et al.

International Search Report for corresponding International Patent Application No. PCT/US2007/003620, dated Jul. 11, 2007, 4 pgs.

Black et al., "Unsaturated Fatty Acids. Part I. The Synthesis of Erythrogenic (Isantic) and Other Acetylenic Acids," Journal of the Chemical Society, Abstracts (1953), pp. 1785-1793.

(Continued)

*Primary Examiner* — Anthony J Green
(74) *Attorney, Agent, or Firm* — Brinks Hofer Gilson & Lione

(57) ABSTRACT

The invention provides surface coating compositions comprising a preservative comprising 9-decenoic acid, salts of 9-decenoic acid, esters of 9-decenoic acid, or combinations thereof. The surface coating compositions may be water-based coatings (e.g., a latex paint) or solvent-based coatings (e.g., a solvent-based paint). The surface coating compositions may be paints, stains, varnishes, concrete coatings, anti-graffiti coatings, and the like. Methods for protecting a surface coating composition from in-can spoilage and protecting a coating of the surface coating composition from deterioration by the action of microorganisms are also described.

57 Claims, 4 Drawing Sheets

U.S. PATENT DOCUMENTS

| | | | |
|---|---|---|---|
| 6,599,548 B2 | 7/2003 | Blyth et al. |
| 6,616,922 B2 | 9/2003 | Taylor et al. |
| 6,620,854 B2 | 9/2003 | Schnyder et al. |
| 6,696,597 B2 | 2/2004 | Pederson et al. |
| 6,699,825 B2 | 3/2004 | Rees et al. |
| 6,699,907 B1 | 3/2004 | Dee et al. |
| 6,717,030 B2 | 4/2004 | Messing et al. |
| 6,770,677 B2 | 8/2004 | Carlson et al. |
| 6,794,534 B2 | 9/2004 | Grubbs et al. |
| 6,805,963 B2 | 10/2004 | Janssen et al. |
| 6,838,544 B2 | 1/2005 | Li et al. |
| 6,844,302 B1 | 1/2005 | Boden et al. |
| 6,846,846 B2 | 1/2005 | Modak et al. |
| 6,903,061 B2 | 6/2005 | Masschelein et al. |
| 6,908,628 B2 | 6/2005 | Herruzo Cabrera |
| 6,939,840 B2 | 9/2005 | Lichtenberg et al. |
| 6,951,834 B2 | 10/2005 | Mitra et al. |
| 6,956,120 B2 | 10/2005 | Ikewaki et al. |
| 7,102,047 B2 | 9/2006 | Grubbs et al. |
| 7,341,983 B2 | 3/2008 | Pedersen et al. |
| 2001/0055644 A1 | 12/2001 | Kirby et al. |
| 2002/0032241 A1 | 3/2002 | Schnyder et al. |
| 2002/0034568 A1 | 3/2002 | Blyth et al. |
| 2002/0103094 A1 | 8/2002 | Masschelein et al. |
| 2003/0017132 A1 | 1/2003 | Li et al. |
| 2003/0070691 A1 | 4/2003 | Giletto et al. |
| 2003/0194443 A1 | 10/2003 | Yano et al. |
| 2004/0023822 A1 | 2/2004 | Ochs et al. |
| 2004/0082579 A1 | 4/2004 | Pritchard et al. |
| 2004/0138107 A1 | 7/2004 | Fardis et al. |
| 2004/0204596 A1 | 10/2004 | Potier et al. |
| 2004/0247783 A1* | 12/2004 | Rosano .......................... 427/180 |
| 2005/0003994 A1 | 1/2005 | Ochs et al. |
| 2005/0058610 A1 | 3/2005 | Baschong et al. |
| 2005/0058689 A1 | 3/2005 | McDaniel |
| 2005/0070750 A1 | 3/2005 | Newman et al. |
| 2005/0075368 A1 | 4/2005 | Dewis et al. |
| 2005/0084545 A1 | 4/2005 | Pipko et al. |
| 2005/0153876 A1 | 7/2005 | Cameron et al. |
| 2005/0154221 A1 | 7/2005 | Lysenko et al. |
| 2005/0159324 A1 | 7/2005 | Man et al. |
| 2005/0164900 A1 | 7/2005 | Masschelein et al. |
| 2005/0164955 A1 | 7/2005 | Gross et al. |
| 2005/0175714 A1 | 8/2005 | Pipko et al. |
| 2007/0010420 A1 | 1/2007 | Lange et al. |
| 2007/0227400 A1 | 10/2007 | Zullo et al. |
| 2007/0269563 A1 | 11/2007 | Mixon et al. |
| 2008/0033026 A1 | 2/2008 | Zullo et al. |
| 2008/0213444 A1 | 9/2008 | Mixon et al. |

FOREIGN PATENT DOCUMENTS

| | | |
|---|---|---|
| EP | 0 564 945 | 10/1993 |
| EP | 0 568 307 | 11/1993 |
| EP | 0 576 691 | 1/1994 |
| EP | 1 276 372 B1 | 1/2003 |
| EP | 1 561 476 | 8/2005 |
| EP | 1 571 182 | 9/2005 |
| JP | 48058125 | 8/1973 |
| JP | 58013776 | 1/1983 |
| JP | 61203183 A * | 9/1986 |
| JP | 2000103726 | 4/2000 |
| KR | 10-2001-0041774 A | 5/2001 |
| WO | WO 2004/050815 | 6/2004 |
| WO | WO 2005/013931 | 2/2005 |
| WO | WO 2005/015996 A1 | 2/2005 |
| WO | WO 2005/089552 | 9/2005 |
| WO | WO 2007/016067 A2 | 2/2007 |
| WO | WO 2008/140469 A2 | 11/2008 |

OTHER PUBLICATIONS

The United States Pharmacopeia (USP) 25th Edition, "<51> Antimicrobial Effectiveness Testing," 2002, pp. 1869-1871.

Pederson, et al., "Adv. Synth. Catal.," 2002, 344, 728.

Michel, et al, "(ω-1)-Flouroalk-(ω-1)-enoic Acids: Potential Fungicides," Inst. Chim. Organique, Univ. Lausanne, Lausanne, Switz. Synthesis (1996) pp. 1007-1011.

International Search Report for International Application No. PCT/US2007/021941, dated Feb. 24, 2009, 3 pages.

International Search Report and International Preliminary Report on Patentability for International Application No. PCT/US2007/003623, dated Mar. 8, 2010, 12 pages.

Office Action from co-pending U.S. Appl. No. 11/704,866, dated Apr. 14, 2010, 12 pages.

International Preliminary Report on Patentability for International Application No. PCT/US2007/003620, dated Aug. 12, 2008, 7 pages.

Kodicek, E., "The Effect of Unsaturated Fatty Acids on Gram-Positive Bacteria," *Symposia of the Society of Experimental Biology*, No. III, 1949, pp. 217-232.

Nieman, C., "Influence of Trace Amounts of Fatty Acids on the Growth of Microorganisms," *Bacteriological Reviews*, vol. 18, Baltimore, MD, 1954, pp. 147-163.

Kabara, Jon J., et al., "Fatty Acids and Derivatives as Antimicrobial Agents," *Antimicrobial Agents and Chemotherapy*, Jul. 1972, pp. 23-28.

Kabara, Jon J., et al., "Antimicrobial Action of Isomeric Fatty Acids on Group A *Stretococcus*," *Journal of Medicinal Chemistry*, vol. 16, No. 9, 1973, pp. 1060-1063.

Kabara, J.J., et al., "Antimicrobial Lipids: Natural and Synthetic Fatty Acids and Monoglycerides," *Lipids*, vol. 12, No. 9, 1977, pp. 753-759.

* cited by examiner

30

32

34

36

38

C823

C827

C627

C712

C697

C682

SURFACE COATING COMPOSITIONS AND METHODS

CROSS-REFERENCE TO RELATED APPLICATIONS

This application claims the benefit of U.S. Provisional Application having Ser. No. 60/772,137, filed Feb. 9, 2006, and entitled SURFACE COATING COMPOSITIONS AND METHODS; and to U.S. Provisional Application having Ser. No. 60/851,472, filed Oct. 13, 2006, and entitled ANTIMICROBIAL COMPOSITIONS, METHODS, AND SYSTEMS, the disclosures of which are incorporated herein by reference.

BACKGROUND

It is well known that surface coatings (e.g., water-based or solvent-based paints, stains, varnishes, anti-graffiti coatings, and the like) are susceptible to attack by microorganisms. Such attack may occur in the wet state (i.e., commonly referred to as "in-can" spoilage) or it may occur on the surface of the surface coating after application to a substrate.

Surface coatings typically contain a number of ingredients that may be susceptible to in-can spoilage by the action of microorganisms. Examples include binder, thickener, and other ingredients such as coalescing agents and defoamers. Water-borne (e.g., latex) paints and coatings are particularly prone to in-can spoilage by microorganisms. Examples of organisms that may cause in-can spoilage include *Alcaligenes* species, *Bacillus* species, *E. coli, Micorococcus luteus, Proteus vulgaricus, Pseudomonas* species, *Candida albicans, Saccharomyces cerevisiase, Aspergillus* species and *Penecillium* species. In-can spoilage may be characterized, for example, by gassing, discoloration, reduced viscosity, ropiness, and phase separation.

After a surface coating composition has been applied to a surface to form a coating, organisms in the environment (e.g., fungi or algae) may begin to grow on the surface of the film if conditions are favorable (e.g., the presence of moisture and humidity). The presence of organisms on the film is undesirable and may result in film degradation, for example, discoloration, dulling, loss of integrity, increased dirt retention, and loss of adhesion of the film. Examples of species that may grow on the dried films include *Aspergillus* sp., *Penecillium* sp., *Cladosporium* sp., *Aurebasidium* sp., *Alternaria* sp., *Mucor* sp., and *Trichoderma*. Yeasts (e.g., *Candida* and *Rhodotorula*) are also found in areas with high humidity, for example, bathrooms.

Mold growth on dried films not only results in the discoloration and disfigurement, but also may contribute to air quality and health issues for the building inhabitants. Surface growth may contribute to "sick-building syndrome" by contributing to the spore load in the air. It is now recognized that fungal spores and bacteria may be allergens and may cause health problems (Reiss, 1986). Some of the symptoms include respiratory problems, skin rashes, heart palpitations, headaches, and chronic fatigue.

In order to provide overall protection, surface coating compositions may comprise two or more preservatives including: (1) an "in-can" preservative for wet-state protection of the surface coating; and (2) a dry film preservative for protection of the dried surface coating.

Desirable properties of the in-can preservative include a broad-spectrum activity, low toxicity, cost effectiveness, quick kill rate, minimal discoloration, low odor, and low partition coefficient. The requirements for the dry film preservative are similar to those for an in-can preservative, except that dry film preservatives are desirably longer-lasting and more effective against fungi than in-can preservatives.

In view of the foregoing, surface coating compositions comprising preservatives that have low toxicity, broad spectrum efficacy including both in-can and dry film efficacy, quick kill rate, minimal discoloration, and low odor are highly desirable.

SUMMARY

In one aspect, the invention provides a surface coating composition comprising a coating-forming component and preservative comprising 9-decenoic acid, a salt of 9-decenoic acid, an ester of 9-decenoic acid, or a combination thereof. The surface coating composition may be a water-based coating (e.g., a latex paint) or it may be a solvent-based coating (e.g., a solvent-based paint). The surface coating composition may be paint, stain, varnish, concrete coating, anti-graffiti coating, and the like. In an exemplary embodiment, the surface coating is a latex paint composition comprising water, a binder, a pigment, and a preservative comprising 9-decenoic acid, a salt of 9-decenoic acid, an ester of 9-decenoic acid, or a combination thereof.

In some embodiments, the surface coating composition comprises a preservative comprising 9-decenoic acid having the structure shown in formula (I):

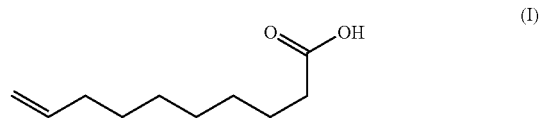

In other embodiments, the surface coating comprises a preservative comprising an ester of 9-decenoic acid having the structure shown in formula (II):

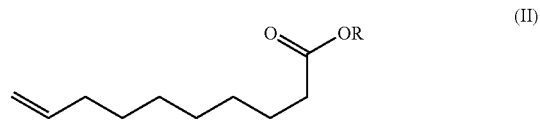

where —R is an organic group, for example, an aliphatic group, such as, an alkyl group, an alkenyl group, an alkynyl group, an alicyclic group, or an aryl group. In an exemplary embodiment, —R is a C1 to C18 alkyl group, for example, methyl, ethyl, propyl (n-propyl or i-propyl) butyl (n-butyl or t-butyl), heptyl, octyl, nonyl, decyl, dodecyl, or octadecyl.

In other embodiments, the surface coating comprises a preservative comprising a salt of 9-decenoic acid having the structure shown in formula (III):

$$K^{+n}[R^-]_n$$

where R⁻ is

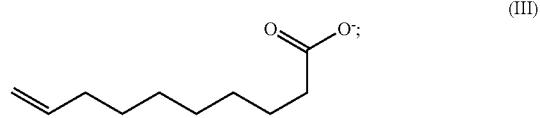

$K^{+n}$ is a positively charged cation having a charge of +n; and +n is an integer from 1 to 2.

When n is 1, representative examples include group IA cations (such as $Li^+$, $Na^+$, $K^+$, and $Ag^+$), and a variety of ammonium salts, such as those including ammonium ($NH_4^+$) or quaternary ammonium ($NR_4^+$) as cations. When n is 2, representative examples include $Ca^{2+}$, $Mg^{2+}$, $Zn^{2+}$, $Cu^{2+}$, and $Fe^{2+}$. When n is 3, representative examples include $Al^{3+}$, $Fe^{3+}$ and $Ce^{3+}$. When n is 4, representative examples include $Ce^{4+}$.

In another aspect, the invention provides a coating comprising a surface coating composition of the invention. The coating may be formed, for example, by applying the surface coating composition of the invention to a substrate and allowing the surface coating to dry and/or cure.

In another aspect, the invention provides a method of coating a surface, the method comprising applying a surface coating composition to a surface to form a durable coating on the surface, wherein the surface coating composition includes a coating-forming component that forms the durable coating and a preservative comprising 9-decenoic acid, a salt of 9-decenoic acid, an ester of 9-denoic acid, or a combination thereof.

In some embodiments, the preservative is added to the coating formulation in an amount ranging from about 0.01% weight to about 5% weight based on the total weight of the coating composition, or about 0.1% to about 1% weight based on the total weight of the coating composition.

In embodiments of the invention, the preservative is prepared by cross-metathesis of ethylene with (a) a triglyceride comprising C9-C10 unsaturated fatty acid esters, (b) a C9-C10 unsaturated fatty acid, (c) a C9-C10 unsaturated fatty ester, or (d) a mixture thereof. The cross-metathesis is typically conducted in the presence of a metathesis catalyst.

In some embodiments the preservative is a highly pure composition comprising, for example, about 90% weight or greater 9-decenoic acid (or ester or salt thereof), about 95% weight or greater 9-decenoid acid (or ester or salt thereof), about 96% weight or greater 9-decenoic acid (or ester or salt thereof), about 97% weight or greater 9-decenoic acid (or ester or salt thereof), about 98% weight or greater 9-decenoic acid (or ester or salt thereof), about 99% weight or greater 9-decenoic acid (or ester or salt thereof), about 99.5% weight or greater 9-decenoic acid (or ester or salt thereof), about 99.8% weight or greater 9-decenoic acid (or ester or salt thereof), or about 99.9% weight or greater 9-decenoic acid (or ester or salt thereof).

In some embodiments, the preservative comprises less than about 0.5% weight 8-nonenoic acid, less than 0.5% weight n-decanoic acid, less than 0.5% weight 3-decenoic acid, or less than 0.5% weight undecenoic acid. In an exemplary embodiment, the preservative comprises less than about 0.5% weight of each of 8-nonenoic acid, n-decanoic acid, 3-decenoic acid, and undecenoic acid.

DETAILED DESCRIPTION

Figure 1:
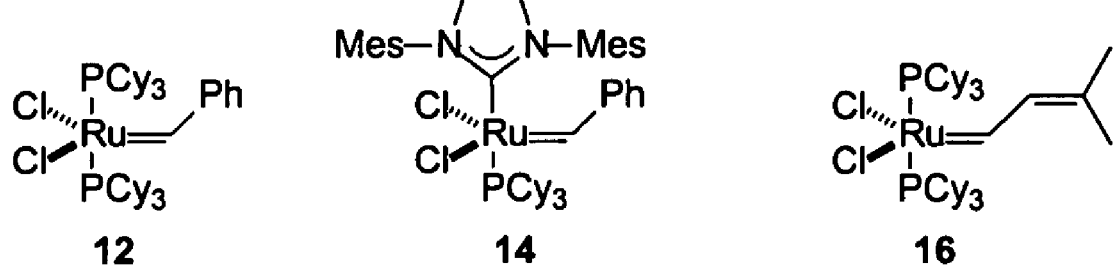
FIG. 1 is a figure showing exemplary ruthenium-based metathesis catalysts.

The present invention relates to surface coatings compositions that are resistant to deterioration resulting from attack by microorganisms. More particularly, in one aspect, the present invention relates to surface coating compositions comprising a coating-forming component and a preservative comprising 9-decenoic acid, an ester of 9-decenoic acid, a salt of 9-decenoic acid, or a mixture thereof.

In some embodiments of the invention the preservative provides resistance to in-can spoilage of the surface coating composition. In other embodiments, the preservative provides resistance to microbial growth on coatings formed from the surface coating composition. In yet other embodiments, the preservative provides resistance to in-can spoilage as well as resistance to microbial growth on coatings formed from the surface coating composition.

Surface coating compositions of the invention comprise a coating-forming component. In many embodiments, the coating-forming component comprises a non-volatile material (e.g., a solid) that dries or cures to form a durable coating when the surface coating composition is applied to a surface. Coating-forming components include polymeric resin binders (e.g., oils, acrylics, alkyds, polyesters resins, and the like), curable binders (e.g., epoxies, acrylates, and the like). Also included in many compositions are pigments, fillers, and the like. In many embodiments, the surface coatings are durable coatings, for example, being formulated for application to surface where the coating will, depending upon the application, remain in place for a substantial time period, for example, several weeks (e.g., an anti-graffiti coatings) to many years (e.g., a paint, clear-coat, stain, or epoxy coating).

Examples of surface coating compositions include water-based surface coatings and solvent-based surface coatings, such as paint (e.g., interior or exterior water-based or solvent-based paint), varnish (e.g., acrylic or polyurethane wood coatings), stains, clear coatings, concrete coatings, anti-graffiti coatings, water-based coatings used for processing paper, textiles, leather, metal, wood and mineral surfaces and the like.

In some embodiments of the invention, the preservative is 9-decenoic acid having the structure shown in formula (I):

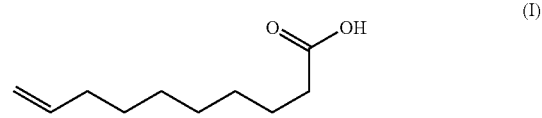

9-decenoic acid has been found to be effective at killing many in-can spoilage microorganisms that may be present in surface coatings. In addition, 9-decenoic acid displays a desirable low toxicity.

Generally, 9-decenoic acid is a colorless liquid having a molecular weight of approximately 170, boiling point of approximately 269° C. to 271° C. at 760 mm, a specific gravity of 0.912 to 0.920 at 25° C., and a refractive index of 1.44 to 1.45 at 20° C. Generally, 9-decenoic acid is soluble in water and in alcohol.

In some embodiments of the invention, the preservative is an ester of 9-decenoic acid having the structure shown in formula (II):

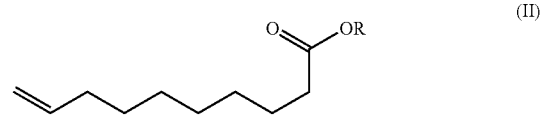

where —R is an organic group. As used herein the term "organic group" includes aliphatic groups, alicyclic groups, and aromatic groups. Organic groups may include heteroatoms (e.g., O, N, or S atoms), as well as functional groups such as carbonyl groups. In the context of the present invention, the term "aliphatic group" means a saturated or unsaturated, linear or branched, hydrocarbon group. This term is used to encompass alkyl, alkenyl, and alkynyl groups. The term "alkyl group" means a monovalent, saturated, linear or branched, hydrocarbon group. The term "alkenyl group" means a monovalent, unsaturated, linear or branched, hydrocarbon group with one or more carbon-carbon double bonds. The term "alkynyl group" means a monovalent, unsaturated, linear or branched, hydrocarbon group with one or more carbon-carbon triple bonds. An alicyclic group is an aliphatic group arranged in one or more closed ring structures. The term is used to encompass saturated (e.g., cycloparaffin) or unsaturated (e.g., cycloolefin or cycloacetylene) groups. An aromatic or aryl group is an unsaturated cyclic hydrocarbon having a conjugated ring structure. Included within aromatic or aryl groups are those possessing both an aromatic ring structure and an aliphatic or alicyclic group.

In some embodiments, —R is an alkyl group, for example, a C1 to C18 alkyl group, a C2 to C18 alkyl group, a C1 to C6 alkyl group, or a C2 to C6 alkyl group. Representative examples include methyl, ethyl, propyl (n-propyl or i-propyl) butyl (n-butyl or t-butyl), heptyl, octyl, nonyl, decyl, dodecyl, octadecyl, and the like. In other embodiments, —R is an alkenyl group, for example, a C9 alkenyl group, such as, —CH$_2$—CH$_2$—CH$_2$—CH$_2$—CH$_2$—CH$_2$—CH$_2$—CH$_2$=CH$_2$.

In some aspects, —R may be selected to serve a dual role as an antimicrobial agent and emulsifier or compatibility aid. For purposes of emulsifying immiscible phases or stabilizing an emulsion, the addition of an amphiphilic molecule may enhance interfacial contact. Amphiphilic molecules are molecules that two regions having distinct polarities. One part of the molecule is polar, or hydrophilic, which makes it attracted to a more polar phase in a system. The other part of the molecule is non-polar, or hydrophobic, making it attracted to a non-polar phase in a system. The dual nature of these molecules draws them to the interface between two immiscible phases where they adsorb and lower the energy of the phase boundary. Molecules that adsorb strongly and provide high interfacial loadings are typically good surfactants, and may be good emulsifiers. The strength of attraction of a surfactant to the interface is dependent, at least in part, on the strength of interaction for each part of the amphiphile to each phase. Accordingly, a strongly adsorbing surfactant will, generally speaking, have a polar hydrophilic component attracted to a polar phase, and a non-polar hydrophobic component attracted to a non-polar phase. A feature of each component of the amphiphile is that it preferably has sufficient solubility as a whole molecule in one of the phases so that it can be delivered to the interface. Interfacial tension is reduced by adsorption of surfactant molecules and is a colligative property, meaning that interfacial tension reduction is dependent primarily on the number of molecules adsorbed.

In the case of linear alkyl groups that are used as a hydrophobic moiety, the chain length is a variable that may be used to tailor the emulsification properties. Chains that are too short may not provide enough attraction to the non-polar phase to make a strongly adsorbing amphiphile. Chains that are too long may bring greater steric hindrance to the interface and may prevent other molecules from adsorbing, thus reducing the interfacial loading and tension reduction. Long alkyl chains may also have reduced solubility in one of the phases. Embodiments where —R is a C8 to C16 alkyl group may provide emulsification properties in certain surface coating compositions. In some embodiments, —R is a C10 to C12 alkyl group. The selection of the appropriate alkyl group may depend, for example, on the nature of the rest of the molecule to which the alkyl group is attached, and may also depend on the composition of the phases with which the molecule interacts.

In some embodiments of the invention, the preservative is a salt of 9-decenoic acid, for example, the salt represented by formula (III):

$$K^{+n}[R^-]_n \quad (III)$$

where $R^-$ is

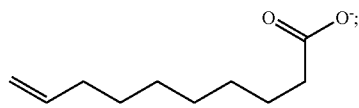

$K^{+n}$ is a positively charged cation having a charge of +n; and +n is an integer, for example, from 1 to 2.

When n is 1, representative examples include group IA cations (such as Li$^+$, Na$^+$, K$^+$, and Ag$^+$), and a variety of ammonium salts, such as those including ammonium (NH$_4^+$) or quaternary ammonium (NR$_4^+$) as cations. When n is 2, representative examples include Ca$^{2+}$, Mg$^{2+}$, Zn$^{2+}$, Cu$^{2+}$, and Fe$^{2+}$. When n is 3, representative examples include Al$^{3+}$, Fe$^{3+}$ and Ce$^{3+}$. When n is 4, representative examples include Ce$^{4+}$. In still further embodiments, the anion/cation pair ($K^{+n}[R^-]_n$) can bind a known antimicrobial agent, such as those described elsewhere herein as useful for the second antimicrobial agent.

In some aspects, utilization of a salt of 9-decenoic acid, as described in Formula (III), can be advantageous, for example, by being more soluble in aqueous systems, less volatile, and/or easier to handle as compared to the acid or ester forms of 9-decenoic acid. The choice of an antimicrobial agent from Formulae (I), (II) and/or (III) will depend upon the end use coating composition, including formulation consideration, target microorganisms, and the like.

Embodiments of the preservative compounds of formulas (I), (II), and (III) may be prepared, for example, by metathesis. In some embodiments, ethylene is cross-metathesized with an unsaturated starting composition comprising (a) a triglyceride comprising C9-C10 unsaturated fatty acid esters, (b) a C9-C10 unsaturated fatty acid, (c) a C9-C10 unsaturated fatty esters, or a mixture thereof. The cross-metathesis is typically conducted in the presence of a metathesis catalyst.

In some embodiments, oleic acid is cross-metathesized with ethylene in the presence of a metathesis catalyst to yield 9-decenoic acid according to equation (IV).

$$CH_3(CH_2)_7CH=CH(CH_2)_7COOH+ \\ CH_2=CH_2 \rightarrow CH_2=CH(CH_2)_7COOH+CH_3 \\ (CH_2)_7CH=CH_2 \quad (IV)$$

In other embodiments, methyl oleate is cross-metathesized with ethylene in the presence of a metathesis catalyst to yield the methyl ester of 9-decenoic acid according to equation (V). Methyl oleate may be obtained commercially, for example, from Cognis Inc. (Cincinnati, Ohio) or from NuChek Prep, Inc. (Elysian, Minn.).

$$CH_3(CH_2)_7CH=CH(CH_2)_7COOCH_3+ \\ CH_2=CH_2 \rightarrow CH_2=CH(CH_2)_7COOCH_3+CH_3 \\ (CH_2)_7CH=CH_2 \quad (V)$$

If the unsaturated starting material is in triglyceride form, it may be first hydrolyzed to form free unsaturated fatty acids, followed by cross-metathesis with ethylene to yield 9-decenoic acid. Alternatively, the triglyceride may be cross-metathesized with ethylene followed by hydrolysis to yield 9-decenoic acid. In yet another embodiment, the triglyceride is cross-metathesized with ethylene followed by transesterification with an alcohol to yield an ester of 9-decenoic acid.

In some embodiments, an α-olefin compound is cross-metathesized with an unsaturated starting composition comprising: (a) a triglyceride comprising C9-C10 unsaturated fatty acid ester, (b) a C9-C10 unsaturated fatty acid, (c) a C9-C10 unsaturated fatty esters, or a mixture thereof. The cross-metathesis is typically conducted in the presence of a metathesis catalyst. Representative examples of α-olefins include 1-butene, 1-propene, 1-pentene, 1-hexene, 1-heptene, 1-octene, and 1-decene. Other α-olefins may also be used. Cross-metathesis of an α-olefin compound with a C9-10 unsaturated fatty acid, ester, or triglyceride yields a mixture of products including 9-decenoic acid, esters of 9-decenoic acid, and other olefins. The composition of the product depends upon the α-olefin compound that is used and the C9-C10 unsaturated fatty acid, ester, or triglyceride that is used as the starting material.

In an exemplary embodiment as shown in equation (VI), methyl oleate is cross-metathesized with 1-propene in the presence of a metathesis catalyst to yield the methyl ester of 9-decenoic acid and the methyl ester of 9-undecenoic acid, along with other olefin compounds. Methyl oleate may be obtained commercially, for example, from Cognis Inc. (Cincinnati, Ohio) or from NuChek Prep, Inc. (Elysian, Minn.).

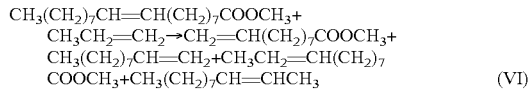

$$CH_3(CH_2)_7CH=CH(CH_2)_7COOCH_3+\\CH_3CH=CH_2 \rightarrow CH_2=CH(CH_2)_7COOCH_3+\\CH_3(CH_2)_7CH=CH_2+CH_3CH=CH(CH_2)_7\\COOCH_3+CH_3(CH_2)_7CH=CHCH_3 \quad (VI)$$

If the unsaturated starting material is in triglyceride form, it may be first hydrolyzed to form free unsaturated fatty acids, followed by cross-metathesis with α-olefin to yield 9-decenoic acid. Alternatively, the triglyceride may be cross-metathesized with an α-olefin followed by hydrolysis to yield 9-decenoic acid. In yet another embodiment, the triglyceride is cross-metathesized with an α-olefin followed by transesterification with an alcohol to yield an ester of 9-decenoic acid. In still another embodiment, the triglyceride is transesterified with an alcohol to yield a fatty ester followed by cross-metathesis with an α-olefin to produce the ester of 9-decenoic acid.

In some embodiments, it is desirable to treat the C9-C10 unsaturated starting composition to reduce its peroxide value (PV) prior to conducting the cross-metathesis reaction. For example, the starting composition may be treated to reduce the peroxide value to about 1 or less. The peroxide value of the starting material may be reduced by treating the starting composition with an adsorbent such as sodium bisulfite, magnesium silicate, sodium borohydride, or combinations thereof. A useful adsorbent is the magnesium silicate commercially under the trade designation "Magnesol" (from Dallas Group of America, Inc.). In order to treat using magnesium silicate, the starting composition is typically heated (e.g., to a temperature of about 80° C.) and stirred while under a nitrogen sparge. After degassing with nitrogen, about 1% weigh to about 5% weight magnesium silicate is added and the composition is stirred for a period of time (e.g., about 1 hour) to allow the magnesium silicate to adsorb impurities from the starting composition. In some embodiments, a filter aid (e.g., "Celite 545" from Sigma-Aldrich) is also added along with the adsorbent. After adsorption, the starting composition is allowed to cool and is filtered one or more times before conducting the cross-metathesis reaction. Prior to performing cross-metathesis, the material is preferably held under nitrogen at freezer temperature (e.g., below about 0° C., more typically between about −10° C. to −20° C.).

Figure 2:
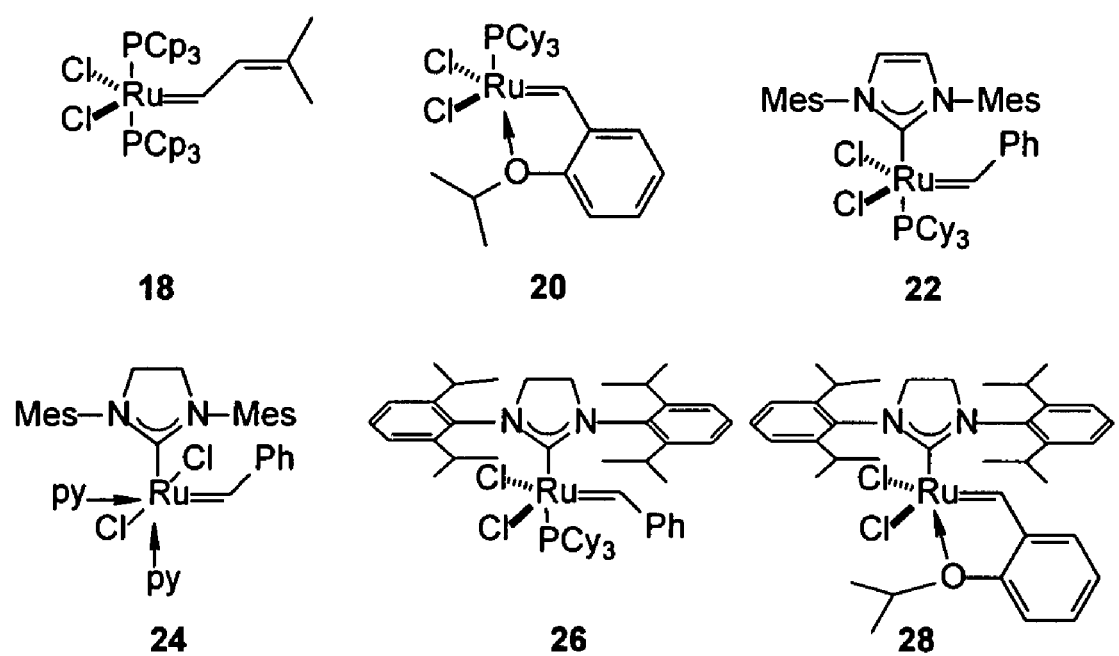
FIG. 2 is a figure showing exemplary ruthenium-based metathesis catalysts.
Figure 3:
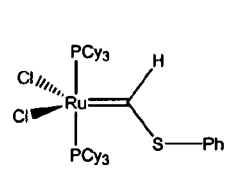
FIG. 3 is a figure showing exemplary ruthenium-based metathesis catalysts.
Figure 3:
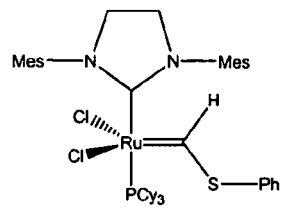
Figure 3:
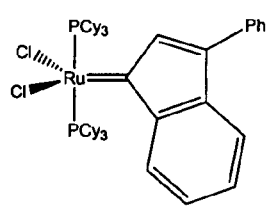
Figure 3:
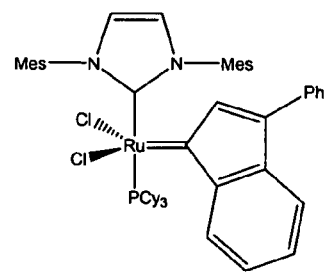
Figure 3:
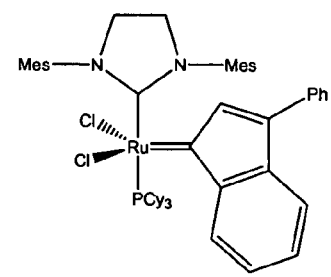
Figure 4:
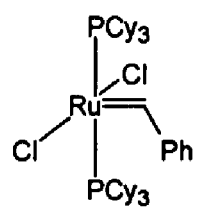
FIG. 4 is a figure showing exemplary ruthenium-based metathesis catalysts.
Figure 4:
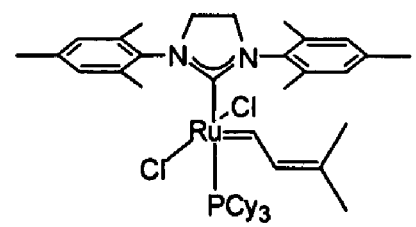
Figure 4:
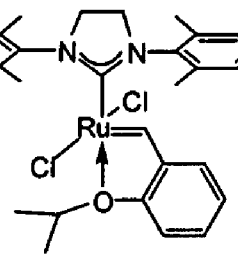
Figure 4:
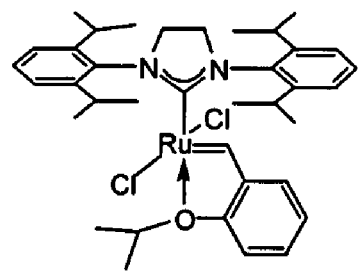
Figure 4:
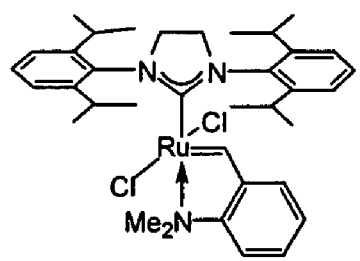
Figure 4:
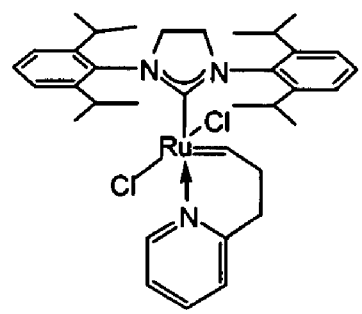

The metathesis reaction is conducted in the presence of a catalytically effective amount of a metathesis catalyst. The term "metathesis catalyst" includes any catalyst or catalyst system that catalyzes a metathesis reaction. Any known or future-developed metathesis catalyst may be used, alone or in combination with one or more additional catalysts. Exemplary metathesis catalysts include metal carbene catalysts based upon transition metals, for example, ruthenium, molybdenum, osmium, chromium, rhenium, and tungsten. Referring to FIG. 1, exemplary ruthenium-based metathesis catalysts include those represented by structures 12 (commonly known as Grubbs's catalyst), 14 and 16. Referring to FIG. 2, structures 18, 20, 22, 24, 26, and 28 represent additional ruthenium-based metathesis catalysts. Referring to FIG. 3, structures 30, 32, 34, 36, and 38 represent additional ruthenium-based metathesis catalysts. Referring to FIG. 4, catalysts C627, C682, C697, C712, and C827 represent still additional ruthenium-based catalysts. In the structures of FIGS. 1-4, Ph is phenyl, Mes is mesityl, py is pyridine, Cp is cyclopentyl, and Cy is cyclohexyl. Techniques for using the metathesis catalysts are known in the art (see, for example, U.S. Pat. Nos. 7,102,047; 6,794,534; 6,696,597; 6,414,097; 6,306,988; 5,922,863; and 5,750,815). Metathesis catalysts as shown, for example, in FIGS. 1-4 are manufactured by Materia, Inc. (Pasadena, Calif.).

Additional exemplary metathesis catalysts include, without limitation, metal carbene complexes selected from the group consisting of molybdenum, osmium, chromium, rhenium, and tungsten. The term "complex" refers to a metal atom, such as a transition metal atom, with at least one ligand or complexing agent coordinated or bound thereto. Such a ligand typically is a Lewis base in metal carbene complexes useful for alkyne- or alkene-metathesis. Typical examples of such ligands include phosphines, halides and stabilized carbenes. Some metathesis catalysts may employ plural metals or metal co-catalysts (e.g., a catalyst comprising a tungsten halide, a tetraalkyl tin compound, and an organoaluminum compound).

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

The metathesis process can be conducted under any conditions adequate to produce the desired metathesis products. For example, stoichiometry, atmosphere, solvent, temperature and pressure can be selected to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the unsaturated polyol ester to catalyst may range from about 5:1 to about 10,000,000:1 or from about 50:1 to 500,000:1. In some embodiments, an amount of about 1 to about 10 ppm, or about 2 ppm to about 5 ppm, of the metathesis catalyst per double bond of the starting composition (i.e., on a mole/mole basis) is used.

The metathesis reaction temperature may be a rate-controlling variable where the temperature is selected to provide a desired product at an acceptable rate. The metathesis temperature may be greater than −40° C., may be greater than about −20° C., and is typically greater than about 0° C. or greater than about 20° C. Typically, the metathesis reaction temperature is less than about 150° C., typically less than about 120° C. An exemplary temperature range for the metathesis reaction ranges from about 20° C. to about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 10 kPa, in some embodiments greater than about 30 kP, or greater than about 100 kPa. Typically, the reaction pressure is no more than about 7000 kPa, in some embodiments no more than about 3000 kPa. An exemplary pressure range for the metathesis reaction is from about 100 kPa to about 3000 kPa.

In some embodiments, the metathesis reaction is catalyzed by a system containing both a transition and a non-transition metal component. The most active and largest number of catalyst systems are derived from Group VIA transition metals, for example, tungsten and molybdenum.

Additional details regarding the production of 9-decenoic acid by metathesis can be found in U.S. Provisional Application Ser. No. 60/851,693, filed Oct. 13, 2006 entitled "Synthesis of Terminal Alkenes From Internal Alkenes Via Olefin Metathesis" and in U.S. Provisional Application Ser. No. 60/851,501, filed Oct. 13, 2006 entitled "Methods of Making Monounsaturated Functionalized Alkene Compounds by Metathesis."

The 9-decenoic acid (or salt or ester thereof) may be separated from the starting material and other components using known techniques for separation including, for example, distillation.

In some embodiments, the preservative comprising 9-decenoic acid (or an ester or salt thereof) that is produced by metathesis is a highly pure composition comprising about 90% weight or greater 9-decenoic acid (or ester or salt thereof), for example, about 95% weight or greater 9-decenoid acid (or ester or salt thereof), about 96% weight or greater 9-decenoic acid (or ester or salt thereof), about 97% weight or greater 9-decenoic acid (or ester or salt thereof), about 98% weight or greater 9-decenoic acid (or ester or salt thereof), about 99% weight or greater 9-decenoic acid (or ester or salt thereof), about 99.5% weight or greater 9-decenoic acid (or ester or salt thereof), about 99.8% weight or greater 9-decenoic acid (or ester or salt thereof), or about 99.9% weight or greater 9-decenoic acid (or ester or salt thereof).

In some embodiments, the preservative comprising 9-decenoic acid (or ester or salt thereof) that is produced by metathesis comprises less than about 0.5% weight 8-nonenoic acid (e.g., less than about 0.1% weight 8-nonenoic acid). In other embodiments, the preservative comprising 9-decenoic acid (or ester or salt thereof) that is produced by metathesis comprises less than about 0.5% weight of n-decanoic acid (e.g., less than about 0.1% weight n-decanoic acid). In other embodiments, the preservative comprising 9-decenoic acid (or ester or salt thereof) that is produced by metathesis comprises less than about 0.5% weight 3-decenoic acid (e.g., less than about 0.1% weight 3-decenoic acid). In other embodiments, the preservative comprising 9-decenoic acid (or ester of salt thereof) that is produced by metathesis comprises less than about 0.5% weight undecenoic acid (e.g., less than about 0.1% weight undecenoic acid).

In one exemplary embodiment, the preservative comprising 9-decenoic acid (or ester or salt thereof) that is produced by metathesis comprises less than about 0.5% weight 8-nonenoic acid, less than about 0.5% weight n-decanoic acid, less than about 0.5% weight 3-decenoic acid, and less than about 0.5% weight undecenoic acid. In another exemplary embodiment, the preservative comprising 9-decenoic acid (or ester or salt thereof) that is produced by metathesis comprises less than about 0.1% weight 8-nonenoic acid, less than about 0.1% weight n-decanoic acid, less than about 0.1% weight 3-decenoic acid, and less than about 0.1% weight undecenoic acid.

Non-metathesis routes to the production of 9-decenoic acid include, for example, the method reported by Black et al., in *Unsaturated Fatty Acids. Part I. The Synthesis of Erythrogenic (Isantic) and Other Acetylenic Acids*; Journal of the Chemical Society, Abstracts (1953) at pp. 1785-93. As reported by Black, a solution of chromium trioxide (19.0 g) in water (20 cc) was added over 1.5 hours with vigorous stirring to a solution of 1:1 diphenylundeca-1:10-diene (25.0 g) in glacial acetic acid (250 cc) at 35° C. After an additional 0.5 hour stirring, acetic acid (70 cc) was removed under reduced pressure, and 2N sulphuric acid (500 cc) was added to the residue. Extraction of the product with benzene and isolation of the acidic fraction yielded 9-decenoic acid (8.5 g).

9-decenoic acid can also be obtained commercially, for example, from Pyrazine Specialties, Inc. (Athens, Ga.). Whether produced by metathesis or another technique, 9-decenoic acid may be converted to its esters (see, formula II) and salts (see, formula III) according to known synthetic techniques for converting carboxylic acid compounds into esters or salts, respectively.

In another aspect, the invention provides a method of protecting a surface coating composition (e.g., a water-based paint or coating) from in-can spoilage or film degradation due to the action of microorganisms. The method comprises incorporating into the surface coating composition a preservative comprising 9-decenoic acid, a salt of 9-decenoic acid, an ester of 9-decenoic acid, or a combination thereof.

In some embodiments, the method protects the surface coating composition from in-can spoilage from the action of microorganisms. In other embodiments, the method protects the surface coating composition from film degradation due to the action of microorganisms. In an exemplary embodiment, the method protects the surface coating composition from both in-can spoilage and film degradation from the action of microorganisms. Film degradation typically take the form of discoloration, dulling, loss of integrity, increased dirt retention, and loss of adhesion of the film.

A preservative for paint film desirably provides protection against both fungal and algal growth. The fact that a preservative is known to possess fungicidal activity, however, does not mean that it will necessarily be effective in inhibiting mold growth on exterior surfaces for long periods of time. For example, certain preservatives may lose their fungicidal activity prior to the surface coating composition being applied to a surface in the form of a coating. Other preservatives may prevent deterioration by anaerobic microorganisms in a sealed can, but may fail to prevent the formation of mold or mildew by aerobic microorganisms on a surface exposed to air. In addition, the activity of the preservative may be impaired by the weathering environment to which most exterior coatings are exposed.

The amount of preservative that is desirable in a given surface coating formulation can be determined by one of skill in the art using various known techniques and methods. Performance of a given preservative in a composition may be evaluated, for example, as described below.

In one technique, the minimum inhibitory concentration (MIC) of the preservative in a surface coating is determined. MIC refers to the concentration of a given preservative below which growth of microorganisms is not inhibited. MIC may be determined using a dilution series to identify the amount of preservative that is required to inhibit microbial growth under defined laboratory conditions. In this test, panels are coated with the preservative containing surface coating and efficacy is determined against a selected grouping of fungal and algal species that are often found on coated surfaces. Representative organisms include, for example, fungi, such as, *Alternaria alternata, Aspergillus* species, *Aureobasidium pullulans, Cladosporium* species, *Penicillium* species, *Phoma violacea, Stachybotrys chartarum*; and algae, such as, *Oscillatoria* spp., *Chlorella* spp., *Trentepohlia* spp., *Nostoc* spp., and *Pleurococcus* spp. MIC values are often presented in parts per million (ppm) required to inhibit the growth of a target organism or group of target organisms. A lower MIC value indicates increased efficacy.

Accelerated laboratory exposure may also be used to evaluate the desired amount of preservative in a coating formulation. This test typically involves placing panels coated with a preservative-containing coating formulation into a test chamber having a humid atmosphere. One or more test microorganisms are added directly to the coating or are introduced into the chamber. The high humidity promotes rapid microbial growth and the samples are monitored over time to determine the effectiveness of the preservative at the formulated level in inhibiting growth of the test organism(s). A representative accelerated exposure protocol is reported in ASTM D3273 "Standard Test Method for Resistance to Growth of Mould on the Surface of Interior Coatings in an Environmental Chamber".

In another method, field trials are conducted in order to determine how a preservative performs in a coating when exposed to outdoor conditions. In such tests, the preservative-containing coating is applied to a test panel and is exposed at a fixed orientation and angle. The panels are monitored over time and are rated for the extent of microbial growth. Performance of the preservative is measured as the time (e.g., in months or years) microbial growth to reach a predetermined level. A representative field trial protocol is reported in ASTM D3456 "Standard Practice for Determining by Exterior Exposure Tests the Susceptibility of Paint Films to Microbiological Attack".

Performance of a preservative for efficacy against in-can spoilage may be evaluated according to several techniques. In one technique, the preservative is evaluated to determine the MIC of the preservative for in-can spoilage of a coating formulation. MIC may be determined using a dilution series to identify the amount of preservative that is required to inhibit in-can microbial growth under defined laboratory conditions. In this test, efficacy is determined against a selected grouping of microorganisms that are known to spoil wet coating compositions. Representative organisms include, for example, bacteria, such as, *Alcaligenes* species, *Micrococcus luteus, Escherichia coli, Proteus vulgaris,* and *Pseudomonas* spp.; fungi, such as, *Alternaria alternata, Aspergillus* spp., *Geotrichum candidum,* and *Penicillium* spp.; and yeast, such as, *Candidia albicans, Rhodotorula rubra,* and *Saccharomyces cerevisiae.* MIC values for in-can spoilage are often presented in parts per million (ppm) required to inhibit the growth of a target organism or group of target organisms.

Another method for evaluating a preservative for in-can preservation of a coating composition is a challenge test. In a challenge test, microorganisms are deliberately added to a sample of the preservative-containing coating formulation. The survival of the microorganism as a function of time is then monitored. In some test protocols, the sample is challenged several times. A representative protocol for evaluating preservative efficacy is ASTM 2574 "Standard Test Method for Resistance of Emulsion Paints in the Container to Attack by Microorganisms."

In some embodiments, the preservative is added to the coating formulation in an amount ranging from about 0.01% weight to about 5% weight based on the total weight of the coating composition, or about 0.1% to about 1% weight based on the total weight of the coating composition. The preservative may be incorporated into the surface coatings using conventional techniques.

In some embodiments, two or more (e.g., 2, 3, 4 or more) preservatives are used in a coating composition of the invention in order to provide, for example, a broader spectrum of activity, lower toxicity, and/or lower cost. For example, two or more of: 9-decenoic acid, salts of 9-decenoic acid, and esters of 9-decenoic acid may be used together in a water-based paint or coating composition of the invention. In some embodiments, one or more of 9-decenoic acid, a salt of 9-decenoic acid, or an ester of 9-decenoic acid may be used with one or more second in-can or dry film preservatives.

Representative examples of in-can preservatives include 4,4-dimethyloxazolidine; 3,4,4,-trimethyloxazolidine; 1,2-dibromo-2,4-dicyanobutane; 2-[(hydroxymethyl)-amino] ethanol; 2-[(hydroxymethyl)-amino]propanol; 1-(3-chlorallyl)-3,5,7-triaza-1-azoniaadamantane chloride; 1,2-benzisothiazolin-3-one; 5-chloro-2-methyl-4-isothiazolin-3-one; 2-methyl-4-isothiazolin-3-one; 5-hydroxymethoxymethyl-1-aza-3,7-dioxa-bicyclo-[3.3.0]octane; 5-hydroxymethyl-1-aza-3, 7-dioxabicyclo-[3.3.0]octane; 5-hydroxypolymethyl-1-aza-3,7-dioxabicyclo[3.3.0]-octane; hexahydro-1,3,5-triethyl-s-triazine; 2-hydroxymethyl-2-nitro-1,3propanediol; chloroacetamide; methyl chloroisothiazolinone; methylisothiazolinone (methyl chloroisothiazolinone and methylisothiazolinone are available under the trade designation "KATHON"); 2,4,4' trichloro-2-hydroxydiphenyl ether (available under the trade designation "TRICLOSAN"); metal salts (e.g., silver chloride or copper nitrate); glycols (e.g., phenoxyethanol); alcohols (e.g., benzylalcohol); quaternary ammonium salts (e.g., benzalkonium chloride); and phenol derivatives (e.g., orthophenyl-phenol).

Representative examples of dry film preservatives include tetrachloroisophthalonitrile, 2-iodo-2-propynyl butyl carbamate, 2-n-octyl-4-isothiazolin-3-one, diiodomethyl-p-tolylsulphone, n-(trimethylthio)phthalimide, carbendazim, dichloro-octylisothiazolinone, zinc pyrithione, thiuram and barium meta-borate. Combinations may be used to gain broad-spectrum efficacy.

In some embodiments, the first preservative and the second preservative are present in ratios ranging from about 1:10 to about 10:1. In other embodiments, the first preservative is added to the coating formulation in an amount ranging from about 0.01% weight to about 5% weight based on the total weight of the coating composition (e.g., about 0.1% to about 1% weight based on the total weight of the coating composition), and the second preservative is added to the coating formulation in an amount ranging from about 0.01% weight to about 5% weight based on the total weight of the coating composition (e.g., about 0.1% to about 1% weight based on the total weight of the coating composition).

In some embodiments, surface coatings of the invention comprise water-based latex paint compositions comprising a latex binder, water, and a preservative comprising 9-decenoic acid, an ester of 9-decenoic acid, a salt of 9-decenoic acid, or a combination thereof. In addition, the surface coating compositions may contain various auxiliary materials, such as pigments, extenders, fillers, thickeners, driers, plasticizers, wetting agents, emulsifying agents, freeze-thaw stabilizers, coalescents, dispersants, anti-settling agents, defoamers, solvents, and the like in the amounts ordinarily used for these purposes. In some embodiments, a second in-can or dry film preservative may be added.

The manufacture of a latex paint typically occurs in two steps, commonly referred to as the grind (step 1) and the letdown (step 2). In the grind, one or more of the liquid components (e.g., water) are mixed together followed by the addition of the dry pigments. The dry pigments are dispersed in the liquid components under high shear. In the letdown stage, the latex binder and other ingredients are added, typically under low speed mixing to form the latex paint composition. A biocidally effective amount of the preservative compound(s) may be added at either the grind stage or the letdown stage, and may be preblended with a component of the composition or may be added directly. In an exemplary embodiment, the preservative(s) is added in the letdown stage.

The invention will now be described with reference to the following non-limiting examples.

EXAMPLES

Example 1

Efficacy of 9-decenoic acid and the methyl ester of 9-decenoic acid against *Pseudomonas aeruginosa* ATCC 15442, *Escherichia coli* O157:H7 ATCC 43895 and *Candida albicans* ATCC 10231 was measured through the determination of the minimum inhibitory concentration (MIC) and minimum bacteriocidal concentration (MBC) using the procedures in the Federal Register, June 1994 and the present NCCLS M11-A4 protocol.

Stock cultures of each organism were transferred onto Mueller-Hinton Agar (MHA) plates and incubated for 24±2 hours at 37±2° C. On the day of the test, the top of at least three to five well-isolated colonies were transferred via wire loop to a tube containing 4 to 5 ml of Trypticase Soy Broth (TSB). The TSB culture was incubated for 2 to 6 hours and turbidity was adjusted with sterile saline to achieve the turbidity of the 0.5 McFarland Standard.

The concentrated 9-decenoic acid was diluted 1:40 in Mueller-Hinton Broth (MHB) to yield a 2.5% stock solution. The test solution of the methyl ester of 9-decenoic acid was formulated in the same manner. For each organism, 12 dilutions of the 9-decenoic acid and the methyl ester of 9-decenoic acid in MHB were prepared ranging from 0.2500 to 0.0005%. A 2-ml aliquot of appropriately diluted 9-decenoic acid or the methyl ester of 9-decenoic acid solution was placed in each tube. Each tube was inoculated with 0.05 ml of a 1:10 dilution of one challenge organism. Tubes were incubated at 37±2° C. for 20-24 hours and observed for growth or no growth. For the MBC, tubes that exhibited no growth were subcultured on Trypticase Soy Agar (TSA) plates and incubated at 37±2° C. for 20-24 hours and observed for growth. Controls were run for sterility, viability and organism confirmation. It was determined that all cultures were viable and pure.

The MIC was defined as the concentration of 9-decenoic acid or the methyl ester of 9-decenoic acid that completely inhibited growth of the challenge organism. The MBC was defined as the concentration of 9-decenoic acid or the methyl ester of 9-decenoic acid that completely eradicated viable organisms from the test system.

TABLE 1

MIC and MBC of 9-decenoic acid and the methyl ester of 9-decenoic acid for organisms listed.

| Test Organism | 9-decenoic acid | | Methyl ester of 9-decenoic acid | |
|---|---|---|---|---|
| | MIC (%) | MBC (%) | MIC (%) | MBC (%) |
| *Pseudomonas aeroginosa*, ATCC 15442 | 0.0625 | 0.1250 | 0.0625 | 0.1250 |
| *Escherichia coli* O157:H7, ATCC 43895 | 0.1250 | 0.1250 | 0.1250 | 0.1250 |
| *Candida albicans*, ATCC 10231 | 0.0625 | 0.0625 | 0.0156 | 0.0156 |

The rate of kill for these organisms upon exposure to 9-decenoic acid was determined using the American Society for Testing and Materials (ASTM) procedure entitled "Standard Test Method for the Assessment of Microbiocidal Activity of Test Materials Using a Time-Kill Procedure", October 1998. This procedure incorporates the recommendations described in the "Manual of Clinical Microbiology,"5$^{th}$ ed., edited by A. B. Balows et al., ASM, Washington, and is directed by the Federal Register, June 1994.

Stock cultures were transferred into TSB and incubated for 18-24 hours at 37±2° C. A second transfer was made onto TSA plates and were incubated for 18-24 hours at 37±2° C. The plates were removed from incubation and the bacterial growth washed from the agar surface using Butterfield's Phosphate Buffered Dilution Water (PBDW). The bacterial suspension was adjusted to contain approximately $10^8$ Colony Forming Units (CFU)/ml with PBDW using spectrophometric methods extant in the laboratory.

The concentrated 9-decenoic acid was diluted 1:40 in filter sterilized isopropanol to yield a 2.5% stock solution. Subsequent dilutions to the 9-decenoic acid stock solutions were made with sterile Deionized Water (DI) to achieve concentrations of 0.1%, 0.05%, 0.01%, and 0.001%. The pH was determined for each dilution; pH values ranged from 4.4-4.1. Additionally, the 9-decenoic acid stock solution was adjusted to pH 7 with 1 N NaOH and serially diluted with sterile DI to achieve concentrations of 1.0%, 0.75% and 0.5%.

Compliant with the ASTM procedure cited, for each challenge microorganism a 9.9 ml aliquot of the prepared 9-decenoic acid suspension was added to a sterile tube. A 0.1 ml aliquot of the standardized inoculum was added to the 9-decenoic acid solution representing the start of the test exposure. The inoculated 9-decenoic acid solution was immediately mixed thoroughly. The inoculated suspension was held at room temperature for 0.5, 2, 5, 7 and 10 minute exposure times for tests run at ~pH 4. The pH 7 tests were held at room temperature for 0.5 and 2 minutes.

At each exposure sample time, a 1.0 ml aliquot of the inoculated 9-decenoic acid suspension was transferred to 9.0 ml of D/E Neutralizing Broth. Additional ten-fold serial dilutions were made in PBDW and plated in duplicate on TSA. All plates were incubated for 48 hours at 37±2° C. and visually examined for growth. The plates are enumerated, recorded and log kill determined for each time point.

The following study controls were conducted: culture purity, neutralizer sterility, initial suspension population, test population, neutralization verification and a negative control using isopropanol. Culture purity was verified by performing a streak plate for isolated colonies on the each culture used. All cultures were determined to be pure based on consistent colony morphology typical for the test organism. The neutralizer sterility was confirmed by no growth in an incubated sample.

The population of the initial and test culture were determined by serial dilution, plating and enumerating after incubation. The initial suspension were determined to be $\geq 10^4$ CFU/ml. The test culture population was used for calculation of the log reduction achieved at each time point.

Neutralization effectiveness was verified by a filtration test. For each organism, four tubes were prepared with 9 ml D/E Neutralizing Broth and fewer than 100 CFU/ml of the organism. A 1.0 ml aliquot of prepared 9-decenoic acid was added to each tube. Immediately, the entire contents of 2 tubes were filtered through a filtration apparatus and rinsed with sterile diluent. The remaining 2 tubes were held at room temperature for 30 minutes and then the entire contents were filtered using the same procedure. The filters were aseptically transferred to TSA plates and incubated for 48 hours at 37±2° C. and visually examined for growth. All neutralizations controls showed effective recovery of the cultures.

To demonstrate any antimicrobial activity of the isopropanol diluent, a 1:40 dilution of sterile deionized water in isopropanol was made and further diluted as done for the 1000 ppm test concentration of 9-decenoic acid. This control was inoculated, subcultured and incubated as in the test procedure. It was determined that the concentrations of isopropanol used did not contribute to the antimicrobial activity of the test given that <1 log reduction was measured with these controls.

TABLE 2

Log reduction of organisms after exposure to 0.01% 9-decenoic acid at pH 4.4.

| | Exposure Time (minutes) | | | | |
|---|---|---|---|---|---|
| Test Organism | 0.5 | 2 | 5 | 7 | 10 |
| Pseudomonas aeruginosa, ATCC 15442 | >6.1 | >6.1 | >6.1 | >6.1 | >6.1 |
| Escherichia coli 0157:H7, ATCC 43895 | 1.3 | 1.6 | 2.2 | 1.8 | 2.7 |
| Candida albicans, ATCC 10231 | 1.0 | 2.9 | >6.7 | >6.7 | >6.7 |

TABLE 3

Log reduction of organisms after exposure to 0.05% 9-decenoic acid at pH 4.1.

| | Exposure Time (minutes) | | | | |
|---|---|---|---|---|---|
| Test Organism | 0.5 | 2 | 5 | 7 | 10 |
| Pseudomonas aeruginosa, ATCC 15442 | >6.1 | >6.1 | >6.1 | >6.1 | >6.1 |
| Escherichia coli 0157:H7, ATCC 43895 | >6.2 | >6.2 | >6.2 | >6.2 | >6.2 |
| Candida albicans, ATCC 10231 | >6.7 | >6.7 | >6.7 | >6.7 | >6.7 |

TABLE 4

Log reduction of organisms after exposure to 0.1% 9-decenoic acid at pH 4.1.

| | Exposure Time (minutes) | | | | |
|---|---|---|---|---|---|
| Test Organism | 0.5 | 2 | 5 | 7 | 10 |
| Pseudomonas aeruginosa, ATCC 15442 | >6.1 | >6.1 | >6.1 | >6.1 | >6.1 |
| Escherichia coli 0157:H7, ATCC 43895 | >6.2 | >6.2 | >6.2 | >6.2 | >6.2 |
| Candida albicans, ATCC 10231 | >6.7 | >6.7 | >6.7 | >6.7 | >6.7 |

TABLE 5

Log reduction of Escherichia coli, ATCC 11229 after exposure to 9-decenoic acid at pH 7.

| | Exposure Time (minutes) | |
|---|---|---|
| 9-decenoic acid concentration (%) | 0.5 | 2 |
| 0.5 | 0 | 0 |
| 0.75 | 0.83 | >4.2 |
| 1.0 | >4.2 | >4.2 |

A time kill test was performed in the same manner with the methyl ester of 9-decenoic acid. The results showed less then 1-log reduction for all organisms after 10 minutes with all concentrations (0.01, 0.05 and 0.1%). Although the methyl ester was not efficacious is this test water system, it was efficacious in liquid complex media (see Table 1). Higher concentrations may be required for effectiveness.

The effectiveness of 9-decenoic acid on Aspergillus and Penecillium which occasionally result in in-can spoilage of paint was determined using the protocol on preservative effectiveness found in the United States Pharmacopeia (USP), 25th Edition, 2002, USP <51>.

Stock cultures of the fungi Aspergillus flavus, ATCC 9170 and Penecillium verrucosum, ATCC 18381 were cultured onto Sabouraud Dextrose Agar (SDA) and incubated at 25-30° C. for at least 1 week. The spores were washed form the agar surface with sterile saline, filtered through sterile glass wool, enumerated and stored under refrigeration for no longer than thirty days. On the day of the test, the suspension was diluted to approximately $10^8$ CFU/ml.

The 9-decenoic acid was diluted in the same manner as previously described to achieve, 0.25, 0.125, 0.0625, 0.03, 0.015, 0.0078 and 0.0039% and dispensed in 20 ml aliquots in sterile test tubes. For each concentration tested, a 0.1 ml aliquot of each inoculum was added to a final concentration of $10^5$ to $10^6$ CFU/ml. The tubes were incubated at room temperature and sampled on days 0, 1, 2, 4, 7, 14, 21 and 28.

At each sample point, 1.0 ml aliquots were withdrawn, serially diluted and plated in triplicate on SDA. The plates were incubated at 25-30° C. for 3-7 days. The colonies were counted and the average CFU/ml was calculated. Controls for purity, viability and sterility were performed as described previously.

According to the US Pharmacopoeia, a test compound is an effective preservative if the concentrations of viable fungi remain at or below the initial concentrations during the first fourteen days and after 28 days. According to this definition, 9-decenoic acid is an effective preservative against *Aspergillus flavus* and *Penecillium verrucosum* at concentrations as low at 0.078%. However, it was found to be fungicidal against *P. verrucosum* after 2 days at 0.15% and after 1 day at 0.03%. For *A. flavus*, 9-decenoic acid was fungicidal at 0.015% after 21 days and at day 0 at 0.03%.

TABLE 6

Log reduction of organisms after exposure to 0.0078% 9-decenoic acid.

| | Exposure Time (days) | | | | | | | |
|---|---|---|---|---|---|---|---|---|
| Test Organism | 0 | 1 | 2 | 4 | 7 | 14 | 21 | 28 |
| Aspergillus flavus, ATCC 9170 | 0.2 | 0.3 | 0.2 | 0.4 | 0.4 | 0.4 | 0.8 | 0.8 |
| Penecillium verrucosum, ATCC 18381 | 0 | 0.1 | 0.8 | 0.8 | 0.8 | 0.8 | 1.8 | 1.9 |

TABLE 7

Log reduction of organisms after exposure to 0.015% 9-decenoic acid.

| | Exposure Time (days) | | | | | | | |
|---|---|---|---|---|---|---|---|---|
| Test Organism | 0 | 1 | 2 | 4 | 7 | 14 | 21 | 28 |
| Aspergillus flavus, ATCC 9170 | 1.2 | 2.9 | 3.1 | 3.9 | 3.9 | 4.8 | 5.1 | 4.8 |
| Penecillium verrucosum, ATCC 18381 | 0.1 | 3.0 | 5.1 | 5.1 | 5.1 | 5.1 | 5.1 | 5.1 |

TABLE 8

Log reduction of organisms after exposure to 0.03% 9-decenoic acid.

| | Exposure Time (days) | | | | | | | |
|---|---|---|---|---|---|---|---|---|
| Test Organism | 0 | 1 | 2 | 4 | 7 | 14 | 21 | 28 |
| Aspergillus flavus, ATCC 9170 | 5.1 | 5.1 | 5.1 | 5.1 | 5.1 | 5.1 | 5.1 | 5.1 |
| Penecillium verrucosum, ATCC 18381 | 3.4 | 5.1 | 5.1 | 5.1 | 5.1 | 5.1 | 5.1 | 5.1 |

TABLE 9

Log reduction of organisms after exposure to 0.0625% 9-decenoic acid.

| | Exposure Time (days) | | | | | | | |
|---|---|---|---|---|---|---|---|---|
| Test Organism | 0 | 1 | 2 | 4 | 7 | 14 | 21 | 28 |
| Aspergillus flavus, ATCC 9170 | 5.1 | 5.1 | 5.1 | 5.1 | 5.1 | 5.1 | 5.1 | 5.1 |
| Penecillium verrucosum, ATCC 18381 | 4.3 | 5.1 | 5.1 | 5.1 | 5.1 | 5.1 | 5.1 | 5.1 |

Example 2

Dry Film Preservative

The efficacy of 9-decenoic acid and the methyl ester of 9-decenoic acid as a dry film preservative was determined through the incubation of *Trichoderma virens* ATCC 9645, *Cladosporium cladosporiodes* ATCC 16022 and *Aureobasidium pullulans* ATCC 12536 in the presence of varying concentrations of 9-decenoic acid or the methyl ester of 9-decenoic acid on an agar surface.

Fungal spores were hydrated overnight in 0.1% Tween 80 and then plated on Potato Dextrose Agar (PDA) and incubated at 25-30° C. for 6 days. The spores were washed from the surface with 5 mls of 0.1% Tween 80 and enumerated.

PDA plates with prepared according to the manufactures instructions through sterilization. The agar was tempered to approximately 50° C. and filter sterilized 9-decenoic acid was added to achieve concentrations of 0.1, 0.5 and 1.0% in the agar. Additionally, one concentration of the methyl ester of 9-decenoic acid (0.5%) was also prepared. The agar was thoroughly mixed and poured into sterile petri plates and allowed to solidify.

The agar plates were inoculated with the spore solution to achieve $10^2$ spores/plate. The plates were incubated at 25-30° C. in Ziploc bags with a wet paper towel to keep the moisture level high. The plates were examined for growth after 4, 7, 16, 24 and 31 days. The percent coverage of growth on the agar surface was recorded at each sample point.

TABLE 10

Percentage coverage of agar surface for *Trichoderma virens* in presence of 9-decenoic acid or the methyl ester of 9-decenoic acid.

| | Exposure Time (days) | | | | |
|---|---|---|---|---|---|
| | 4 | 7 | 16 | 24 | 31 |
| 9-decenoic acid (%) | | | | | |
| 0 | 100 | 100 | 100 | 100 | 100 |
| 0.1 | 0 | 0 | 0 | 0 | 0 |
| 0.5 | 0 | 0 | 0 | 0 | 0 |
| 1.0 | 0 | 0 | 0 | 0 | 0 |
| Methyl ester of 9-decenoic acid (%) | | | | | |
| 0.5 | 60 | 95 | 100 | 100 | 100 |

TABLE 11

Percentage coverage of agar surface for *Cladosporium cladosporiodes* in presence of 9-decenoic acid or the methyl ester of 9-decenoic acid.

| | Exposure Time (days) | | | | |
|---|---|---|---|---|---|
| | 4 | 7 | 16 | 24 | 31 |
| 9-decenoic acid (%) | | | | | |
| 0 | 100 | 100 | 100 | 100 | 100 |
| 0.1 | 0 | 0 | 0 | 0 | 0 |
| 0.5 | 0 | 0 | 0 | 0 | 0 |
| 1.0 | 0 | 0 | 0 | 0 | 0 |
| Methyl ester of 9-decenoic acid (%) | | | | | |
| 0.5 | 10 | 50 | 50 | 50 | 50 |

TABLE 12

Percentage coverage of agar surface for *Aureobasidium pullulans* in presence of 9-decenoic acid or the methyl ester of 9-decenoic acid.

| | Exposure Time (days) | | | | |
|---|---|---|---|---|---|
| | 4 | 7 | 16 | 24 | 31 |
| 9-decenoic acid (%) | | | | | |
| 0 | 100 | 100 | 100 | 100 | 100 |
| 0.1 | 0 | 0 | 0 | 0 | 0 |
| 0.5 | 0 | 0 | 0 | 0 | 0 |
| 1.0 | 0 | 0 | 0 | 0 | 0 |
| Methyl ester of 9-decenoic acid (%) | | | | | |
| 0.5 | 0 | 2.5 | 10 | 50 | 75 |

Results in Tables 10-12 show 9-decenoic acid to be effective against all three organisms at 0.1% for up to 31 days. The methyl ester of 9-decenoic acid was not found to be as effective in this test; the growth of the cultures was only significantly inhibited at day 4 for *Trichoderma* and *Cladosporium* and for 16 days for *Aureobasidium*.

Example 3

The efficacy of antimicrobial compositions in accordance with aspects of the invention against the following organisms was determined as follows. The following organisms were incubated in the presence of varying concentrations of 9-decenoic acid (9-DA) on an agar surface: *Aspergillus parasiticus* (ATCC 56857), *Trichoderma virens* (ATCC 9645), *Aureobasidium pullulans* (ATCC 12536), *Aspergillus flavus* (ATCC 96045), *Cladosporium cladosporiodes* (ATCC 16022), *Aspergillus flavus* (ATCC 5917), *Aspergillus oryzae* (ATCC 10124), *Aspergillus parasiticus* (ATCC 13539), *Ulocladium atrum* (ATCC 52426), *Candida albicans* (ATCC 11651), *Alternaria alternata* (ATCC 52170), *Stachybotrys chartarum* (ATCC 16026), *Aspergillus niger* (ATCC 11414).

The minimum inhibitory concentration (MIC) was defined as the least concentration tested that completely inhibited growth of the organism.

Fungal spores were hydrated in 0.1% Tween 80 and then plated onto Potato Dextrose Agar (PDA) (Difco # 213400; Becton, Dickinson and Company, Sparks, Md.) and incubated at 25-30° C. for six (6) days. The spores were washed from the surface with 5 ml of 0.1% Tween 80 and enumerated. PDA plates were prepared according to the manufacturer's instructions through sterilization. The agar was tempered to approximately 50° C. and was filter sterilized. The antimicrobial composition (9-DA) was added by percent weight to molten autoclaved PDA media, with consideration of specific gravity (0.915 g/mL for 9-DA) and purity (98% for 9-DA). The agar was thoroughly mixed and poured into sterile petri plates and allowed to solidify.

The pH of all concentrations of 9-DA percentages in PDA media used was as follows:

TABLE 13

| Media | PH |
|---|---|
| PDA | 5.68 |
| 1.0% 9-DA | 4.62 |
| 0.1% 9-DA | 5.39 |
| 0.05% 9-DA | 5.44 |
| 0.025% 9-DA | 5.53 |

The MIC for 9-DA are shown in Table 14 below:

TABLE 14

MIC for Antimicrobial Compositions.

| Microorganism (ATCC number) | 9-DA MIC (%) |
|---|---|
| *Aspergillus parasiticus* 56857 | 0.05 |
| *Aureobasidium pullulans* 12536 | 0.01 |
| *Aspergillus flavus* 96045 | 0.05 |
| *Aspergillus flavus* 5917 | 0.05 |
| *Aspergillus oryzae* 10124 | 0.05 |
| *Aspergillus parasiticus* 13539 | 0.05 |
| *Ulocladium atrum* 52426 | 0.025 |
| *Candida albicans* 11651 | 0.025 |
| *Aspergillus niger* 11414 | 0.05 |

The agar plates were inoculated with the spore solution to achieve $10^2$ spores/plate. The plates were incubated at 25-30° C. in Ziploc bags with a wet paper towel to keep the moisture level high. The plates were examined for growth at 1, 2, 3, 4, 8, 11, 15, 17, 23, 29 and 31 days. The percent coverage of growth on the agar surface was recorded at each sample point.

For all fungal strains tested above, 9-DA was observed to be an effective antimicrobial agents with MICs in the ranges of 0.01% to 0.05% and 0.01% to 0.1% respectively.

Example 4

Efficacy of the potassium salt of 9-DA was determined through incubation of the following organisms in the presence of varying concentrations of the potassium salt: *Pseudomonas straminea* ATCC 33636, *Bacillus subtilis* ATCC 6051, *Bacillus licheniformis* ATCC 14580, *Bacillus cereus* ATCC 14579, *Pediococcus acidilactici* ATCC 8042, and *Lactobacillus casei* ATCC 334.

Stock cultures of each organism were transferred into MRS liquid medium. MRS medium (Difco 288130) was purchased from Becton, Dickinson and Company, Sparks, Md.

The efficacy of different levels of the potassium salt of 9-DA was tested depending on the organism to inhibit the growth of various microorganisms indicated above.

The selected organisms were incubated overnight in 5 ml of MRS medium at 35° C. and 250 rpm. MRS media with K-9-DA was prepared, along with a control of straight media (no antimicrobial added). The concentrated antimicrobial agents were diluted with the appropriate media required for the respective microorganisms, to reach the required concentrations for the studies as indicated below. The antimicrobial agents were added by weight/volume percent on an 'as 9-DA' basis to the media. The purity of the antimicrobial agent (99% for K-9-DA) was taken into account. The pH of the medium was not adjusted. The target for initial cell density was $10^5$ to $10^6$ cfu/ml. According to the McFarland standard, 0.01 $OD_{600}$ is equivalent to approximately $10^8$ cfu/ml. To achieve the proper dilution, 30 μl of overnight culture diluted to 0.01 $OD_{600}$ was added to the 3 ml of media in each tube. The tubes were incubated at 35° C. Treatments were all done in duplicate. All strains were shaken at 250 rpm, with the exception of *Lactobacillus* (because it is anaerobic). $OD_{600}$ readings were taken at 0, 4, 17, 23 and 47 hours. "Percent reduction in comparison with control" was defined as (1−abs. of treatment/abs. of control)×100. Results are illustrated in the Table 15 below:

TABLE 15

| Organism | w/v % antimicrobial | Abs. at 600 nm for control | Potassium-9 Decenoic Acid | |
|---|---|---|---|---|
| | | | Abs at 600 nm | % reduction in growth vs. control |
| Pseudomonas straminea | 0% control | 6.080 | | |
| | 0.075% 9-DA from K9-DA | | 0.165 | 97.3 |
| | 0.05% 9-DA from K9-DA | | 0.190 | 96.9 |
| Bacillus subtilis | 0% control | 5.730 | | |
| | 0.075% 9-DA from K9-DA | | 0.094 | 98.4 |
| | 0.05% 9-DA from K9-DA | | 0.157 | 97.3 |
| Bacillus licheniformis | 0% control | 2.635 | | |
| | 0.1% 9-DA from K9-DA | | 0.023 | 99.1 |
| | 0.075% 9-DA from K9-DA | | 0.300 | 88.6 |
| Bacillus cereus | 0% control | 5.655 | | |
| | 0.1% 9-DA from K9-DA | | 0.216 | 96.2 |
| | 0.075% 9-DA from K9-DA | | 0.093 | 98.4 |
| Pediococcus acidilactici | 0% control | 5.775 | | |
| | 0.05% 9-DA from K9-DA | | 0.224 | 96.1 |
| | 0.025% 9-DA from K9-DA | | −0.038 | 100.0 |
| Lactobacillus casei | 0% control | 6.835 | | |
| | 0.075% 9-DA from K9-DA | | 0.211 | 96.9 |
| | 0.05% 9-DA from K9-DA | | 0.461 | 93.3 |

All grown in MRS
n = 2 for all

Within the above table, complete growth inhibition is highlighted in bold font for the particular microorganisms and composition tested. In addition, it can be seen that with the exception of *Bacillus licheniformis*, all concentrations of the potassium salt of 9-DA resulted in at least a 95% reduction in growth when compared to the appropriate controls cultivated in MRS medium in the absence of any antimicrobial compound. In the case of *B. licheniformis*, 0.075% potassium 9-DA resulted in an 88.63% reduction in growth when compared with the appropriate control as described above.

It should be noted that MRS medium is considered to be a rich medium by those skilled in the art and one would expect the potassium salt of 9-DA to be even more effective in sub-optimal culture conditions for the various microorganisms tested. Thus it is expected that even greater reductions in growth when compared with growth could be observed with even lower concentrations of the antimicrobial compounds that those listed above.

Example 5

Efficacy of potassium salt of 9-DA were tested at various pH levels against the following: *Bacillus cereus* ATCC 14579, *Pediococcus acidolactici* ATCC 8042, *Pseudomonas straminea* ATCC 33636, and *Lactobacillus casei* ATCC 334. Stock cultures of each organism were transferred into MRS liquid medium. MRS medium (Difco 288130) was purchased from Becton, Dickinson and Company, Sparks, Md. The efficacy of the potassium salt of 9-DA (K-9-DA) was tested at different concentrations and pH levels, including 6.75 (unadjusted), 7.5, and 8.5. The selected organisms were incubated overnight in 5 ml of MRS medium at 35° C. and 250 rpm. MRS media with K-9-DA was prepared, along with a control of straight media (no antimicrobial added). The antimicrobial agent was added by weight/volume percent to the media. The purity, 99% for K-9-DA, was taken into account. The pH adjustments to 7.5 and 8.5 were done with 50% potassium hydroxide. Filter sterilization was used instead of autoclaving to prevent adverse chemical reactions at higher pH and temperature. The target for initial cell density was $10^5$ to $10^6$ cfu/ml. According to the McFarland standard, 0.01 $OD_{600}$ is equivalent to approximately $10^8$ cfu/ml. To achieve the proper dilution, 30 μl of overnight culture diluted to 0.01 $OD_{600}$ was added to the 3 ml of media in each tube. The tubes were incubated at 35° C. with the exception of *Pseudomonas* strains which were incubated at 30° C. Treatments were all done in duplicate. All strains were shaken at 250 rpm, with the exception of *Lactobacillus* (because it is anaerobic). $OD_{600}$ readings were taken at 0, 19, 25.5, 42.5 and 49 hours.

"Percent reduction in growth vs. control" was defined as (1−abs. of treatment/abs. of control)×100. Results are illustrated in the Tables 16-19 below:

TABLE 16

| Organism *Pseudomonas straminea* | Potassium-9 Decenoic Acid 0.075% w/v (as 9-DA) % reduction in growth vs. control |
|---|---|
| Non-pH adjusted | 98.6 |
| pH 7.5 | 96.2 |
| pH 8.5 | 93.9 |

TABLE 17

| Organism *Bacillus cereus* | Potassium-9 Decenoic Acid 0.1% w/v (as 9-DA) % reduction in growth vs. control |
|---|---|
| Non-pH adjusted | 96.5 |
| PH 7.5 | 96.2 |
| PH 8.5 | 93.9 |

TABLE 18

| Organism<br>*Pediococcus<br>acidilactici* | Potassium-9<br>Decenoic Acid<br>0.05% w/v (as 9-DA)<br>% reduction in<br>growth vs. control |
|---|---|
| Non-pH adjusted | 90.6 |
| pH 7.5 | 93.2 |
| pH 8.5 | 95.6 |

TABLE 19

| Organism<br>*Lactobacillus casei* | Potassium-9<br>Decenoic Acid<br>0.075% w/v (as 9-DA)<br>% reduction in<br>growth vs. control |
|---|---|
| Non-pH adjusted | 88.4 |
| pH 7.5 | 91.7 |
| pH 8.5 | 97.7 |

Results indicated that in the case of all organisms tested above, in Tables 16-19, at the concentrations of the antimicrobial agent used (indicated in the table above), the various concentrations of potassium salt of 9-DA tested, resulted in a 92% to 96% reduction in growth at pH 7.5 when compared with the appropriate control organisms grown at the same pH. Various concentrations of the potassium salt of 9-DA tested resulted in a 94% to 98% reduction in growth at pH 8.5 when compared with the appropriate control organisms grown at the same pH.

Based on the observations in Tables 16-19, it is expected that increasing the potassium 9-DA concentration would be required for complete inhibition of growth of those microorganisms that did not show complete growth inhibition at the concentrations of antimicrobial used in this study.

It should also be noted that these studies were performed in rich media under optimal growth conditions for the various microorganisms. Therefore in some cases the use of lower amounts of the antimicrobial could be efficacious in various products or applications where inhibition of specific microbes is desired.

Further, it is surprising that the potassium salt of 9-DA exhibited significant antimicrobial activity at pH levels of 8 and higher. Typically, it has been observed that effectiveness for conventional antimicrobial agents fails around neutral pH levels. Thus, in accordance with some aspects of the invention, the antimicrobial compositions can provide significant benefits over known antimicrobial agents, in light of this additional pH range of efficacy.

The following procedures are applicable to Examples 7-10.

General Procedure for Metathesis Reactions

To a Fisher Porter tube containing metathesis catalyst and degassed internal olefin (e.g., SBO, methyl canola or methyl soyate) is added terminal olefin (e.g., 1-propene or 1-butene). A Fisher Porter tube pressure rated for 225 psi is used. Temperature, catalyst loading and pressure of alpha olefin are indicated in the tables. Metathesis catalyst is removed as described below. Products (e.g., methyl 9-decenoate and methyl 9-undecenoate) are isolated, after trans-esterification in the case of SBO, by fractional vacuum distillation. Excess 1-propene is optionally recovered and recycled in another metathesis reaction.

Catalyst Removal Procedure

A 1.0 M solution of tris(hydroxymethyl)phosphine (THMP) in IPA (25 mol equiv of THMP per mole of metathesis catalyst) is added to the metathesized oil and the mixture is heated at 70° C. for 6 hours under an atmosphere of argon (R. L. Pederson; I. M. Fellows; T. A. Ung; H. Ishihara; S. P Hajela *Adv. Syn. Cat.* 2002, 344, 728). Hexanes is added if needed to form a second phase; the mixture is washed 3 times with water. The organic phase is dried with anhydrous $Na_2SO_4$, filtered and analyzed by GC analysis.

Alternative Catalyst Removal Procedure

A 1.0 M solution of tris(hydroxymethyl)phosphine (THMP) in IPA (25 mol equiv of THMP per mole of metathesis catalyst) is added to the metathesized oil and the mixture is heated at 70° C. for 6 hours under an atmosphere of argon (R. L. Pederson; I. M. Fellows; T. A. Ung; H. Ishihara; S. P Hajela *Adv. Syn. Cat.* 2002, 344, 728). IPA is then removed via rotary evaporator (also removing in part the volatile terminal olefins). Bleaching clay (Pure Flow B80 CG, 5 wt % to product) is added to the crude reaction mixture, which is then stirred overnight under argon at 70° C. The crude product mixture containing the clay is subsequently filtered through a packed bed of sand (10 g), Celite filter aid (5 g), bleaching clay (12.5 g), and sand (10 g). The filtered oil is analyzed by GC analysis.

Example Procedure for the Transesterification of Metathesized SBO

A glass 3-necked round bottom flask containing a magnetic stirrer and fitted with a condenser, temperature probe, and gas adapter was charged with crude metathesized SBO product (~2 L) and 1% w/w NaOMe in MeOH. The resulting light yellow heterogeneous mixture was stirred at 60° C. for 1 hr. Towards the end of the hour, the mixture turned a homogeneous orange color. Esterified products were transferred into a separatory funnel and extracted with 2.0 L DI-$H_2O$. The aqueous layer was then extracted with 2×2.0 L $Et_2O$. The combined organic extracts were dried over anhydrous $Na_2SO_4$ (300 g) for 20 hours. The solution of esterified products was filtered and the filtrate was stripped of solvent via rotary evaporator.

Vacuum Distillation

A glass 2.0 L 3-necked round bottom flask with a magnetic stirrer, packed column, distillation head, and temperature controller was charged with methyl ester products and placed in a heating mantle. The flask was attached to a 2-inch×36-inch glass distillation packed column contain 0.16" Pro-Pak™ stainless steel saddles. The distillation column was adapted to a fractional distilling head, which was connected to a vacuum line. A 500 mL pre-weighed round bottom flask was used for collecting the fractions. Vacuum on this system was <1 mmHg.

GC Analysis Conditions

The products were analyzed using an Agilent 6890 gas chromatography (GC) instrument with a flame ionization detector (FID). The following conditions and equipment were used:

| Column: | Rtx-5, 30 m × 0.25 mm (ID) × 0.25 μm film thickness. |
|---|---|
| Manufacturer: | Restek |
| GC and column conditions: | Injector temperature: 250° C.<br>Detector temperature: 280° C. |
| Oven temperature: | Starting temperature: 100° C., hold time: 1 minute.<br>Ramp rate 10° C./min to 250° C.,<br>hold time: 12 minutes. |
| Carrier gas: | Helium |
| Mean gas velocity: | 31.3 ± 3.5% cm/sec (calculated) |
| Split ratio: | ~50:1 |

The products were characterized by comparing peaks with known standards, in conjunction with supporting data from mass spectrum analysis (GCMS-Agilent 5973N). GCMS analysis was accomplished with a second Rtx-5, 30 m×0.25 mm (ID)×0.25 μm film thickness GC column, using the same method as above. Table 19 provides GC retention times used for identifying compounds in the examples provided below. Table 22 also provides compound abbreviations that are used throughout the examples.

TABLE 22

GC Analysis of Products from the Cross Metathesis of Seed Oils with 1-Propene and 1-Butene.

| Retention Time (min) | Compound | Compound Abbreviation |
|---|---|---|
| 2.039 | 1-Decene | $1C_{10}$ |
| 2.907 | E-2-Undecene | $E\text{-}2C_{11}$ |
| 3.001 | Z-2-Undecene | $Z\text{-}2C_{11}$ |
| 5.298 | Methyl 9-Decenoate | $9C_{10}O_2Me$ (9-DA) |
| 6.708 | Methyl E-9-Undecenoate | $E\text{-}9C_{11}O_2Me$ (9UDA) |
| 6.852 | Methyl Z-9-Undecenoate | $Z\text{-}9C_{11}O_2Me$ (9UDA) |

Example 7

Propenolysis of SBO

SBO (source: Cargill, lot #F5L19) was reacted according to the general metathesis procedure provided above. Catalyst 827 and propene (130 psi) were used, and the reaction was performed at 60° C. The results are provided in Table 23.

TABLE 23

Propenolysis of SBO[1]

| Exp. # | Amt. Catalyst (ppm) | Time (h) | $1C_{10}$ (%) | $E\text{-}2C_{11}$ + $Z\text{-}2C_{11}$ (%) | 9-DA (%) | 9UDA (%) | Yield (%) | $TON_{9\text{-}DA}$ |
|---|---|---|---|---|---|---|---|---|
| 112A | 75 | 2 | 7.14 | 6.13 | 12.72 | 9.49 | 35.74 | 1696 |
| 112B | 75 | 4 | 6.63 | 4.74 | 16.76 | 10.95 | 39.08 | 2234 |
| 113A | 50 | 2 | 7.52 | 5.55 | 15.97 | 10.80 | 39.84 | 3194 |
| 113B | 50 | 4 | 8.99 | 5.38 | 21.61 | 12.30 | 48.29 | 4322 |
| 114A | 25 | 1 | 7.65 | 6.01 | 18.51 | 14.50 | 46.64 | 7403 |
| 114B | 25 | 2 | 7.31 | 6.33 | 18.70 | 16.05 | 48.39 | 7482 |
| 114C | 25 | 3 | 8.71 | 6.58 | 20.69 | 15.56 | 51.54 | 8275 |
| 114D | 25 | 4 | 8.91 | 6.60 | 21.52 | 15.82 | 52.86 | 8609 |
| 116B | 10 | 1 | 2.91 | 2.92 | 4.71 | 4.73 | 15.27 | 4705 |
| 116C | 10 | 2 | 5.68 | 4.77 | 9.50 | 8.35 | 28.30 | 9501 |
| 116D | 10 | 3 | 7.82 | 5.84 | 14.21 | 10.63 | 38.51 | 14214 |
| 116E | 10 | 4 | 7.89 | 5.40 | 15.59 | 10.89 | 39.77 | 15593 |
| 116F | 10 | 6 | 9.53 | 6.42 | 16.42 | 10.74 | 43.11 | 16423 |

[1]Percentages correspond to GC area

Example 8

Propenolysis of Methyl Soyate

Methyl soyate (source: Chemol) was reacted according to the general metathesis procedure provided above. Catalyst 827 and propene (130 psi, unless specified otherwise) were used, and the reaction was performed at 60° C. The results are provided in Table 24.

TABLE 24

Propenolysis of Methyl Soyate[1]

| Exp. # | Amt. Catalyst (ppm) | Time (h) | $1C_{10}$ (%) | $E\text{-}2C_{11}$ + $Z\text{-}2C_{11}$ (%) | 9-DA (%) | 9UDA (%) | Yield (%) | $TON_{9\text{-}DA}$ |
|---|---|---|---|---|---|---|---|---|
| 107[2] | 75 | 4 | 5.60 | 4.79 | 9.96 | 8.15 | 28.23 | 1292 |
| 109 | 75 | 4 | 6.82 | 5.56 | 11.89 | 8.84 | 33.11 | 1585 |
| 111A | 25 | 1 | 10.51 | 7.73 | 22.39 | 15.68 | 56.30 | 8955 |
| 111B | 25 | 2 | 10.78 | 7.51 | 22.51 | 15.10 | 55.90 | 9006 |
| 111C | 25 | 3 | 11.06 | 7.35 | 23.72 | 14.89 | 57.01 | 9486 |
| 111D | 25 | 4 | 11.47 | 7.40 | 23.68 | 14.88 | 57.42 | 9470 |
| 115A | 10 | 0.5 | 8.67 | 6.42 | 16.36 | 11.54 | 42.99 | 16359 |
| 115B | 10 | 1 | 9.78 | 6.40 | 18.90 | 12.13 | 47.21 | 18898 |
| 115C | 10 | 2 | 10.08 | 6.43 | 19.87 | 12.33 | 48.71 | 19871 |
| 115D | 10 | 3 | 10.20 | 6.41 | 20.00 | 12.32 | 48.92 | 20001 |
| 115E | 10 | 4 | 10.17 | 6.43 | 20.13 | 12.36 | 49.10 | 20134 |
| 115F | 10 | 6 | 10.12 | 6.45 | 20.35 | 12.39 | 49.31 | 20347 |
| 117A | 5 | 1.5 | 0.76 | 0.92 | 1.01 | 0.53 | 3.22 | 2020 |
| 117B | 5 | 4 | 0.82 | 0.99 | 1.07 | 1.01 | 3.89 | 2140 |

TABLE 24-continued

Propenolysis of Methyl Soyate[1]

| Exp. # | Amt. Catalyst (ppm) | Time (h) | $1C_{10}$ (%) | $E-2C_{11} + Z-2C_{11}$ (%) | 9-DA (%) | 9UDA (%) | Yield (%) | $TON_{9-DA}$ |
|---|---|---|---|---|---|---|---|---|
| 118A | 2.5 | 1.5 | 0.18 | 0.23 | 0.22 | 0.21 | 0.84 | 880 |
| 118B | 2.5 | 4 | 0.21 | .027 | 0.27 | 1.01 | 1.76 | 1080 |

[1]Percentages correspond to GC area.
[2]Reaction performed with 100 psi propene.

Example 9

Propenolysis of FAMEs

Fatty acid methyl esters (FAMEs) were reacted according to the general metathesis procedure provided above. Canola FAME (source: Cognis, Lot #MF-CNF6C27), SBO FAME (source: Chemol, Lot #IF-24298), and Sun FAME (source: Nu Chek, Lot #"Special") were used. Catalyst 827 (5 ppm) and propene (130 psi) were used, and the reaction was performed at 60° C. The results are provided in Table 25.

TABLE 25

Propenolysis of Various FAMEs[1]

| Exp. # | Seed Oil | Time (h) | $1C_{10}$ (%) | $2C_{11}$ (%) | 9-DA (%) | 9UDA (%) | Yield (%) | $TON_{9-DA}$ |
|---|---|---|---|---|---|---|---|---|
| 018A | Canola FAME | 2 | 10.53 | 7.59 | 16.75 | 11.39 | 46.26 | 33500 |
| 018B | Canola FAME | 4 | 10.42 | 7.56 | 16.93 | 11.47 | 46.38 | 33860 |
| 019A | Canola FAME | 2 | 10.9 | 7.64 | 16.97 | 11.38 | 46.89 | 33940 |
| 019B | Canola FAME | 4 | 11.09 | 7.85 | 17.82 | 11.85 | 48.61 | 35640 |
| 021A | SBO FAME | 2 | 0.77 | 0.98 | 0.98 | 0.94 | 3.67 | 1960 |
| 021B | SBO FAME | 4 | 0.72 | 0.95 | 0.96 | 0.92 | 3.55 | 1920 |
| 022A | Sun FAME | 2 | 0.51 | 0.61 | 0.56 | 0.61 | 2.29 | 1120 |
| 022B | Sun FAME | 4 | 0.5 | 0.6 | 0.55 | 0.62 | 2.27 | 1100 |
| 023A | Sun FAME | 2 | 3.1 | 3.21 | 3.3 | 3.16 | 12.77 | 6600 |
| 023B | Sun FAME | 4 | 2.79 | 3.02 | 3.21 | 3.14 | 12.16 | 6420 |

[1]Percentages correspond to GC area.

Example 10

Propenolysis of FAMEs

Fatty acid methyl esters (FAMEs) were reacted according to the general metathesis procedure provided above. Canola FAME (source: Cognis), SBO FAME (source: Cognis), and Sun FAME (source: Nu Chek) were used. Propene (130 psi) was used as the terminal olefin, and the reaction was performed at 60° C. for 4 hours. The results are provided in Table 26.

TABLE 26

Propenolysis of FAMEs[1]

| Exp. # | Seed Oil | Catalyst (ppm) | $1C_{10}$ (%) | $2C_{11}$ (%) | 9-DA (%) | 9UDA (%) | Yield (%) | $TON_{9-DA}$ |
|---|---|---|---|---|---|---|---|---|
| 012B | Sun FAME | C827 (25) | 18.65 | 13.65 | 21.32 | 15.16 | 68.78 | 8528 |
| 014B | Canola FAME | C827 (25) | 13.19 | 9.63 | 20.78 | 14.91 | 58.51 | 8312 |
| 013B | Sun FAME | C827 (10) | 15.45 | 10.64 | 23.95 | 14.63 | 64.67 | 23950 |
| 015B | Canola FAME | C827 (10) | 13.41 | 8.69 | 20.72 | 13.48 | 56.3 | 20720 |
| 018B | Canola FAME | C827 (5) | 10.42 | 7.56 | 16.93 | 11.47 | 46.38 | 33860 |
| 019B | Canola FAME | C827 (5) | 11.09 | 7.85 | 17.82 | 11.85 | 48.61 | 35640 |

TABLE 26-continued

Propenolysis of FAMEs[1]

| Exp. # | Seed Oil | Catalyst (ppm) | $1C_{10}$ (%) | $2C_{11}$ (%) | 9-DA (%) | 9UDA (%) | Yield (%) | $TON_{9-DA}$ |
|---|---|---|---|---|---|---|---|---|
| 006B[2] | SBO FAME | C848 (25) | 8.67 | 4.38 | 27.52 | 13.39 | 53.96 | 11008 |
| 009B[2] | Canola FAME | C848 (25) | 15.19 | 9.65 | 25.74 | 15.68 | 66.26 | 10296 |

[1]Percentages correspond to GC areas.
[2]Reactions performed at 40° C.

Example 11

Magnesol Purification Technique

This treatment reduces the peroxide value (PV) in the seed oil starting material prior to propenolysis conditions.
Materials:
300 g FAME
2.5% Magnesol adsorbent (1% and 5% also used)
1.25% Celite 545 filter aid; (EM Science lot AD42050)
2-125 mL narrow mouth amber jars
1-60 ml amber jar
Whatmann #4 and #2 filter paper
Nitrogen
Apparatus:
A 3-necked 500 mL round bottom flask with stir bar, thermocouple, controller, heating mantel, nitrogen sparge needle with mineral oil filled bubbler, Buchner funnel and flask was used.
Procedure:
1. The flask was filled with 300 grams of FAME.
2. The stir bar was started.
3. A nitrogen sparge was started.
4. The FAME was heated to 80° C.
5. The FAME was held for 45 minutes to degas.
6. 2.5 wt % Magnesol adsorbent, and 1.5 wt % Celite filter aid were added to the degassed FAME.
7. The resulting composition was held for 1 hour to allow the Magnesol to adsorb.
8. The heating mantel was removed.
9. When the temperature reached 40° C. the nitrogen sparge was stopped.
10. The resulting composition was filtered through #4 paper on a Buchner funnel.
11. After filtering with #4 paper, the composition was filtered twice through Buchner funnel fitted with #2 filter paper.
12. The filtered composition was placed in amber bottles and was sparged with nitrogen for 5 minutes followed by 1 minute blanketing of the headpace with nitrogen.
13. The jars were capped and sealed and were stored in a freezer.

Propenolysis Reaction

Fisher Porter vessels and regulators (valves opened) were brought into a glovebox along with a 10 ml volumetric flask. Seed oil or Soy FAME (10 to 20 g) was pipetted into Fisher Porter vessels. A stock catalyst solution was made in a volumetric flask using methylene chloride, and the appropriate concentration added to the Fisher Porter vessels. The vessels were attached to the regulator heads and the valves were closed. The equipment was removed from the glovebox and was hooked up to a steel manifold with propene feed or straight to small propene tank. After clearing the lines with propene (line is loosely attached to fisher porter head), the lines were tightened onto the head and the solution was sparged three times with propene by allowing it to pressurize to 130 psi and venting. The solution was then pressurized again to 130 psi and was closed and heated to 60° C. with stirring. As the catalyst consumes the propene, the solution was continually brought back to 130 psi by opening and closing the valve. Closing the valve prevents any backflow into the gas cylinder if it is not outfitted with a regulator. Reactions were quenched and metathesis catalyst removed after four hours as described below.

Catalyst Removal Procedure

A 1.0 M solution of tris(hydroxymethyl)phosphine (THMP) in IPA (25 mol equiv of THMP per mole of metathesis catalyst) was added to the metathesized oil and the mixture was heated at 70° C. for 6 hours (under argon) (R. L. Pederson; I. M. Fellows; T. A. Ung; H. Ishihara; S. P Hajela *Adv. Syn. Cat.* 2002, 344, 728). Hexane was added if needed to formed a second phase when the mixture washed 3 times with water. The organic phase was dried with anhydrous $Na_2SO_4$, filtered and analyzed by GC analysis.

Transesterification of Metathesized SBO

To a glass 3-necked round bottom flask with a magnetic stirrer, condenser, temperature probe, and a gas adapter was charged with crude metathesized SBO product (~2 L) and 1% w/w NaOMe in MeOH. Resulted light yellow heterogeneous mixture was stirred at 60° C. for 1 hr. Towards the end of the hour, the mixture turned a homogeneous orange color. Esterified products were transferred into the separatory funnel and extracted with 2.0 L DI-$H_2O$. The aqueous layer was then extracted with 2×2.0 L $Et_2O$. The combined organic extracts were dried over 300 g. of anhydrous $Na_2SO_4$ for 20 hours. The solution of esterified products was filtered and the filtrate was stripped of solvent via rotary evaporator.

Vacuum Distillation

A glass 2.0 L 3-necked round bottom flask with a magnetic stirrer, packed column, distillation head, and temperature controller was charged with methyl ester products and placed in the heating mantle. The flask was attached to a 2-inch×36-inch glass distillation packed column contain 0.16" Pro-Pak™ stainless steel saddles. Distillation column was adapted to a fractional distilling head, which was connected to the vacuum line; a 500 mL pre-weighed round bottom flask was collecting the fractions. Vacuum on this system was <1 mmHg.

GC Analysis Conditions and Methods

The products were analyzed using an Agilent 6890 gas chromatography (GC) instrument with a flame ionization detector (FID). The following conditions and equipment were used:

| | |
|---|---|
| Column: | Rtx-5, 30 m × 0.25 mm (ID) × 0.25 μm film thickness. |
| Manufacturer: | Restek |
| GC and column conditions: | Injector temperature: 250° C. Detector temperature: 280° C. |
| Oven temperature: | Starting temperature: 100° C., hold time: 1 minute. Ramp rate 10° C./min to 250° C., hold time: 12 minutes. |
| Carrier gas: | Helium |
| Mean gas velocity: | 31.3 ± 3.5% cm/sec (calculated) |
| Split ratio: | ~50:1 |

The products were characterized by comparing peaks with known standards, in conjunction with supporting data from mass spectrum analysis (GCMS-Agilent 5973N). GCMS analysis was accomplished with a second Rtx-5, 30 m×0.25 mm (ID)×0.25 μm film thickness GC column, using the same method as above. The Compound Abbreviations are used through the following Tables.

TABLE 27

GC Analysis of Products from the Cross Metathesis of Seed Oils with 1-Propene or 1-Butene.

| Ret Time | Compound | Compound Abbreviation |
|---|---|---|
| 1.300 | E-2-Octene | $2C_8$ |
| 1.596 | 3-Nonene | $3C_9$ |
| 2.039 | 1-Decene | $1C_{10}$ |
| 2.907 | E-2-Undecene | $E\text{-}2C_{11}$ |
| 3.001 | Z-2-Undecene | $Z\text{-}2C_{11}$ |
| 3.836 | 3-Dodecenes | $3C_{12}$ |
| 5.298 | Methyl 9-Decenoate | $9C_{10}O_2Me$ (9-DA) |
| 6.708 | Methyl E-9-Undecenoate | $E\text{-}9C_{11}O_2Me$ (9UDA) |
| 6.852 | Methyl Z-9-Undecenoate | $Z\text{-}9C_{11}O_2Me$ (9UDA) |
| 7.419 | Pentadecadienes | $nC_{15}$ |
| 7.816 | Methyl E-9-Dodecenoate | $E\text{-}9C_{12}O_2Me$ |
| 7.894 | Methyl Z-9-Dodecenoate | $Z\text{-}9C_{12}O_2Me$ |
| 10.939 | 9-Octadecene | $9C_{18}$ |
| 11.290 | Methyl 9-12 tetradecadienoate | $9,12C_{14}O_2Me$ |
| 12.523 | Methyl palmitate | $C_{16}O_2Me$ |
| 14.306 | Methyl linoleates | $9,12C_{18}O_2Me$ |
| 14.363 | Methyl oleates | $9C_{18}O_2Me$ |
| 14.537 | Methyl stearate | $C_{18}O_2Me$ |
| 17.138 | Methyl 9,21-Henicosadienaote | $9,12C_{18}O_2Me$ |
| 17.586 | 1,18 Dimethyl ester of 9-Ocadecene | $9,12C_{18}O_2Me$ |
| 22.236 | Methyl 9,12,15-docosatrienoate | $9,12,15C_{21}O_2Me$ |

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following embodiments.

What is claimed is:

1. A surface coating composition comprising:
   a coating-forming component; and
   a preservative comprising 9-decenoic acid, a salt of 9-decenoic acid, an ester of 9-decenoic acid, or a combination thereof;
   wherein the coating composition has a pH of at least 6.75; and
   wherein the preservative provides anti-microbial activity against gram-negative bacteria, gram-positive bacteria, mold, fungi, and algae, in the coating composition; and
   wherein the surface coating is a latex paint comprising a binder and pigment.

2. The surface coating composition of claim 1, wherein the preservative is a salt of 9-decenoic acid according to formula (III):

$$K^{+n}[R^-]_n \qquad (III)$$

TABLE 28

Propenolysis of Treated SBO and Soy FAMEs (20 g) for 4 hours at 60° C.

| Exp# | Oil | Lot # | Cat ppm | Treatment | % $1C_{10}$ | % $2C_{11}$ | % 9-DA | % 9UDA | C18:0 | $TON_{9\text{-}DA}$ | $TON_{total}$ | 9-DA/C18:0 |
|---|---|---|---|---|---|---|---|---|---|---|---|---|
| 129-108A | Soy FAME | B6 | C827(10) | Magnesol [1] | 8.33 | 5.24 | 24.90 | 16.38 | 5.58 | 24900 | 54850 | 4.46 |
| 129-108D | " | " | C827(5) | Magnesol [1] | 8.07 | 4.92 | 24.06 | 13.95 | 5.63 | 48120 | 102000 | 4.27 |
| 129-108E | " | " | C827(2.5) | Magnesol [1] | 6.99 | 4.45 | 20.08 | 11.97 | 5.62 | 80320 | 173960 | 3.57 |
| 129-108F | " | " | C827(1) | Magnesol [1] | 7.47 | 5.10 | 19.22 | 12.10 | 5.21 | 192200 | 438900 | 3.69 |
| 129-108B | Biodiesel | B7 | C827(10) | Magnesol [2] | 8.27 | 5.28 | 25.17 | 15.65 | 5.44 | 25170 | 54370 | 4.63 |
| 129-108G | " | " | C827(5) | Magnesol [2] | 8.21 | 5.00 | 23.45 | 13.39 | 5.55 | 46900 | 100100 | 4.23 |
| 129-108H | " | " | C827(2.5) | Magnesol [2] | 5.52 | 3.95 | 14.68 | 9.31 | 5.49 | 58720 | 133840 | 2.67 |
| 129-108I | " | " | C827(1) | Magnesol [2] | 2.98 | 2.15 | 5.38 | 4.34 | 5.12 | 53800 | 148500 | 1.05 |
| 129-108C | " | B8 | C827(10) | Magnesol [1] | 8.14 | 5.23 | 24.48 | 14.96 | 5.58 | 24480 | 52810 | 4.39 |
| 129-108J | " | " | C827(5) | Magnesol [1] | 7.43 | 4.59 | 20.88 | 11.95 | 5.34 | 41760 | 89700 | 3.91 |
| 129-108K | " | " | C827(2.5) | Magnesol [1] | 5.04 | 4.33 | 10.64 | 7.49 | 5.07 | 42560 | 110000 | 2.10 |
| 129-108L | " | " | C827(1) | $NaHSO_3$ | 4.67 | 4.22 | 9.16 | 6.84 | 5.02 | 91600 | 248900 | 1.82 |
| 129-108M | " | C5 | C827(10) | Magnesol [2] | 7.95 | 5.04 | 24.37 | 14.89 | 5.14 | 24370 | 52250 | 4.74 |
| 129-108N | SBO | D1 | C827(10) | Magnesol [2] | 7.89 | 4.83 | 24.25 | 14.25 | 5.15 | 24250 | 51220 | 4.71 |
| 129-108O | " | D4 | C827(10) | Magnesol [2] | 7.15 | 5.55 | 20.15 | 15.67 | 5.31 | 20150 | 48520 | 3.79 |

[1] Added 2.5 wt % Magnesol.
[2] Added 5.0 wt % Magnesol.

where R³¹ is

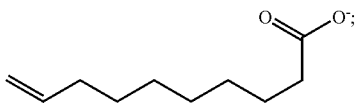

n is an integer ranging from 1 to 2; and
$K^{+n}$ is a +n charged cation.

3. The surface coating composition of claim 2, wherein $K^{+n}$ is selected from the group consisting of $Li^+$, $Na^+$, and $K^+$, $Ag^+$, $NH_4^+$, or quaternary ammonium.

4. The surface coating composition of claim 2, wherein $K^{+n}$ is selected from the group consisting of $Ca^{+2}$, $Mg^{+2}$, $Zn^{+2}$, $Cu^{+2}$, and $Fe^{+2}$.

5. The surface coating of claim 1, wherein the preservative is present in an amount ranging from about 0.01% to about 5.0% by weight.

6. The surface coating of claim 1, wherein the preservative is present in an amount ranging from about 0.1% to about 1.0% by weight.

7. The surface coating of claim 1, wherein the preservative comprises: a first preservative comprising 9-decenoic acid, an ester of 9-decenoic acid, or a salt of 9-decenoic acid; and a second preservative selected from the group consisting of 4,4-dimethyloxazolidine; 3,4,4,-trimethyloxazolidine; 1,2-dibromo-2,4-dicyanobutane; 2[(hydroxymethyl)-amino]ethanol; 2-[(hydroxymethyl)-amino]propanol; 1-(3-chlorallyI)-3,5,7-triaza-1-azoniaadamantane chloride; 1,2-benzisothiazolin-3-one; 5-chloro-2-methyl-4-isothiazolin-3-one; 2-methyl-4-isothiazolin-3-one; 5-hydroxymethoxy-methyl-1-aza-3,7-dioxa-bicyclo-[3.3.0]octane; 5-hydroxymethyl-1-aza-3,7-dioxabicyclo -[3.3.0]octane; 5-hydroxypolymethyl-1-aza-3,7-dioxabicyclo[3.3.0]-octane; hexahydro-1,3,5-triethyl-s-triazine; 2-hydroxymethyl-2-nitro-1,3 propanediol; chloroacetamide; methyl chloroisothiazolinone; methylisothiazolinone; 2,4,4 'trichloro-2-hydroxydiphenyl ether; metal salts; glycols; alcohols; quaternary ammonium salts; phenol derivatives; tetrachloroisophthalonitrile, 2-iodo-2-propynyl butyl carbamate, 2-n-octyl-4-isothiazolin-3-one, diiodomethyl-p-tolylsulphone, n-(trimethylthio)phthalimide, carbendazim, dichlorooctylisothiazolinone, zinc pyrithione, thiuram; and barium meta-borate.

8. The surface coating of claim 7, wherein the first preservative is present in an amount ranging from about 0.01% to about 5% weight and the second preservative is present in an amount ranging from about 0.01% to about 5% weight.

9. The surface coating of claim 8, wherein the preservative comprises about 90% weight or greater 9-decenoic acid or an ester or a salt thereof.

10. The surface coating composition of claim 8, wherein the preservative comprises less than about 0.5% weight undecenoic acid.

11. The surface coating composition of claim 8, wherein the preservative comprises less than about 0.5% weight 8-nonenoic acid, less than about 0.5% n-decanoic acid, less than about 0.5% weight 3-decenoic acid, and less than about 0.5% weight undecenoic acid.

12. The surface coating of claim 8, wherein the preservative comprises about 99% weight or greater 9-decenoic acid or an ester or a salt thereof.

13. The surface coating of claim 8, wherein the preservative comprises about 99.8% weight or greater 9-decenoic acid or an ester or a salt thereof.

14. The surface coating composition of claim 8, wherein the preservative comprises less than about 0.5% weight 8-nonenoic acid.

15. The surface coating composition of claim 8, wherein the preservative comprises less than about 0.5% weight n-decanoic acid.

16. The surface coating composition of claim 8, wherein the preservative comprises less than about 0.5% weight 3-decenoic acid.

17. The surface coating of claim 1, wherein the preservative is formed by metathesis.

18. The surface coating of claim 17, wherein the preservative is formed by cross-metathesis of ethylene or an α-olefin with a starting material comprising:
(a) a triglyceride comprising C9-C10 unsaturated fatty acid esters, (b) a C9-C10 unsaturated fatty acid, (c) a C9-C10 unsaturated fatty ester, or (d) a mixture thereof.

19. The surface coating of claim 18, wherein the α-olefin is 1-propene, 1-butene, 1-pentene, 1-hexene, 1-heptene, 1-octene, 1-decene, and mixtures thereof.

20. The surface coating of claim 18, wherein the starting material is treated with an adsorbent prior to cross-metathesis.

21. The surface coating of claim 20, wherein the adsorbent comprises sodium bisulfite, magnesium silicate, sodium borohydride, or combinations thereof.

22. The surface coating of claim 21, wherein the starting material has a peroxide value of about 1 or less.

23. The surface coating composition of claim 1 wherein the surface coating composition has a neutral or alkaline pH.

24. The surface coating composition of claim 1 wherein the surface coating composition has a pH of at least 7.5.

25. The surface coating composition of claim 1 wherein the surface coating composition has a pH of at least 8.

26. The surface coating composition of claim 1 wherein the surface coating composition has a pH of at least 8.5.

27. A surface coating composition comprising:
a coating-forming component; and
a preservative;
wherein the coating composition has a pH of at least 6.75; and
wherein the preservative provides anti-microbial activity against gram-negative bacteria, gram-positive bacteria, mold, fungi, and algae, in the coating composition;
wherein the preservative is a salt of 9-decenoic acid according to formula (III):

$$K^{+n}[R^-]_n \qquad \text{(III)}$$

where $R^-$ is 

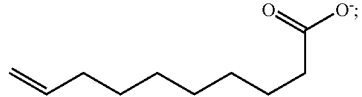

n is an integer ranging from 1 to 2; and
$K^{+n}$ is a +n charged cation
wherein $K^{+n}$ is selected from the group consisting of $Al^{+3}$, $Fe^{+3}$ and $Ce^{+3}$.

28. A method of coating a surface, the method comprising applying a surface coating composition to a surface to form a coating on the surface,
wherein the surface coating composition includes a coating-forming component that forms the coating and a preservative comprising 9-decenoic acid, a salt of 9-decenoic acid, an ester of 9-denoic acid, or a combination thereof;
wherein the coating composition has a pH of at least 6.75;
wherein the preservative provides anti-microbial activity against gram-negative bacteria, gram-positive bacteria, mold, fungi, and algae, in the coating composition; and
wherein the surface coating composition is a latex paint comprising a binder and pigment.

29. The method of claim 28, wherein the preservative provides the coating antimicrobial properties to resist deterioration of the coating by the action of a microorganism.

30. The method of claim 28, wherein the preservative provides the surface coating composition antimicrobial properties to resist in-can spoilage.

31. The method of claim 28, wherein the preservative is 9-decenoic acid.

32. The method of claim 28, wherein the preservative is an ester of 9-decenoic acid according to formula (II):

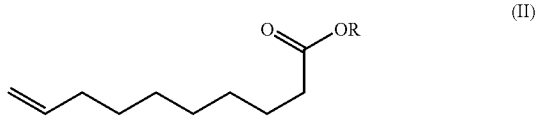

(II)

where —R is an organic group.

33. The method of claim 32, wherein —R is an aliphatic group or an aryl group.

34. The method of claim 32, wherein —R is a C1 to C18 alkyl group.

35. The method of claim 32, wherein —R is methyl, ethyl, propyl, butyl, heptyl, octyl, nonyl, decyl, dodecyl, or octadecyl.

36. The method of claim 32, wherein —R is a C8 to C16 alkyl group.

37. The method of claim 28 wherein the preservative is a salt of 9-decenoic acid according to formula (III):

$$K^{+n}[R^-]_n$$ (III)

where $R^-$ is

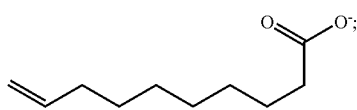

where $K^{+n}$ is a +n charged cation; and
n is an integer ranging from 1 to 2.

38. The method of claim 37, wherein $K^{+n}$ is selected from the group consisting of $Li^+$, $Na^+$, and $K^+$, $Ag^+$, $NH_4^+$, or quaternary ammonium.

39. The method of claim 37, wherein $K^{+n}$ is selected from the group consisting of $Ca^{+2}$, $Mg^{+2}$, $Zn^{+2}$, $Cu^{+2}$, and $Fe^{+2}$.

40. The method of claim 28, wherein the preservative is present in an amount ranging from about 0.01% to about 5% weight.

41. The method of claim 28, wherein the preservative is present in an amount ranging from about 0.1% to about 1% weight.

42. The method of claim 28, wherein the preservative comprises: a first preservative comprising 9-decenoic acid, an ester of 9-decenoic acid, or a salt of 9-decenoic acid; and a second preservative selected from the group consisting of 4,4-dimethyloxazolidine; 3,4,4,-trimethyloxazolidine; 1,2-dibromo-2,4-dicyanobutane; 2[(hydroxymethyl)-amino] ethanol; 2-[(hydroxymethyl)-amino]propanol; 1-(3-chlorallyl) -3,5,7-triaza-1-azoniaadamantane chloride; 1,2-benzisothiazolin-3-one; 5-chloro-2-methyl -4-isothiazolin-3-one;2-methyl-4-isothiazolin-3-one; 5-hydroxymethoxymethyl-1-aza-3,7-dioxa-bicyclo-[3.3.0]octane; 5-hydroxymethyl-1-aza-3,7-dioxabicyclo-[3.3.0 ]octane; 5-hydroxypolymethyl-1-aza-3,7-dioxabicyclo[3.3.0]-octane; hexahydro-1,3,5-triethyl-s -triazine; 2-hydroxymethyl-2-nitro-1,3 propanediol; chloroacetamide; methyl chloroisothiazolinone; methylisothiazolinone; 2,4,4'trichloro-2-hydroxydiphenyl ether; metal salts; glycols; alcohols; quaternary ammonium salts; phenol derivatives; tetrachloroisophthalonitrile, 2-iodo-2-propynyl butyl carbamate, 2-n-octyl-4-isothiazolin-3-one, diiodomethyl-p-tolylsulphone, n-(trimethylthio)phthalimide, carbendazim, dichloro -octylisothiazolinone, zinc pyrithione, thiuram; and barium metaborate.

43. The method of claim 42, wherein the first preservative is present in an amount ranging from about 0.01% weight to about 5% weight and the second preservative is present in an amount ranging from about 0.01% weight to about 5% weight.

44. The method of claim 28, wherein the preservative is formed by metathesis.

45. The method of claim 44, wherein the preservative is formed by cross-metathesis of ethylene or an α-olefin with a starting material comprising: (a) a triglyceride comprising C9-C10 unsaturated fatty acid esters, (b) a C9-C10 unsaturated fatty acid, (c) a C9-C10 unsaturated fatty ester, or (d) a mixture thereof.

46. The method of claim 45, wherein the α-olefin is 1-propene, 1-butene, 1-pentene, 1-hexene, 1-heptene, 1-octene, 1-decene, and mixtures thereof.

47. The method of claim 45, wherein the starting material is treated with an adsorbent prior to cross-metathesis.

48. The method of claim 47, wherein the adsorbent comprises sodium bisulfite, magnesium silicate, sodium borohydride, or combinations thereof.

49. The method of claim 48, wherein the starting material has a peroxide value of about 1 or less.

50. The method of claim 44, wherein the preservative comprises about 90% weight or greater 9-decenoic acid or an ester or a salt thereof.

51. The method of claim 44, wherein the preservative comprises about 99% weight or greater 9-decenoic acid or an ester or a salt thereof.

52. The method of claim 44, wherein the preservative comprises about 99.8% weight or greater 9-decenoic acid or an ester or a salt thereof.

53. The method of claim 44, wherein the preservative comprises less than about 0.5% weight 8-nonenoic acid.

54. The method of claim 44, wherein the preservative comprises less than about 0.5% weight n-decanoic acid.

55. The method of claim 44, wherein the preservative comprises less than about 0.5% weight 3-decenoic acid.

56. The method of claim 44, wherein the preservative comprises less than about 0.5% weight undecenoic acid.

57. A method of coating a surface, the method comprising applying a surface coating composition to a surface to form a coating on the surface,
wherein the surface coating composition includes a coating-forming component that forms the coating and a preservative comprising 9-decenoic acid;
wherein the coating composition has a pH of at least 6.75;
wherein the preservative provides anti-microbial activity against gram-negative bacteria, gram-positive bacteria, mold, fungi, and algae, in the coating composition;
wherein the salt is 9-decenoic acid according to formula (III):

$$K^{+n}[R^-]_n \qquad (III)$$

where $R^-$ is

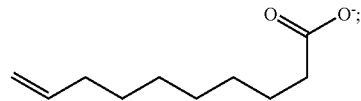

where $K^{+n}$ is a +n charged cation; and
n is an integer ranging from 1 to 2; and
wherein $K^{+n}$ is selected from the group consisting of $Al^{3+}$, $Fe^{3+}$, and $Ce^{3+}$.

* * * * *